US006274342B1

(12) United States Patent
Gutierrez-Ramos et al.

(10) Patent No.: US 6,274,342 B1
(45) Date of Patent: Aug. 14, 2001

(54) NUCLEIC ACID MOLECULES ENCODING MONOCYTE CHEMOTACTIC PROTEIN 5 (MCP-5) MOLECULES AND USES THEREFOR

(75) Inventors: Jose-Carlos Gutierrez-Ramos, Marblehead; Gui-Quan Jia; Jose-Angel Gonzalo, both of Cambridge, all of MA (US)

(73) Assignee: Center for Blood Research, Inc., Boston, MA (US)

( * ) Notice: Subject to any disclaimer, the term of this patent is extended or adjusted under 35 U.S.C. 154(b) by 0 days.

(21) Appl. No.: 08/744,419

(22) Filed: Nov. 8, 1996

Related U.S. Application Data

(60) Provisional application No. 60/026,882, filed on Sep. 18, 1996.

(51) Int. Cl.$^7$ .............................. C07K 14/52; C12N 5/10; C12N 15/19; C12N 15/64
(52) U.S. Cl. ......................... 435/69.5; 435/69.7; 435/6; 435/71.1; 435/71.2; 435/471; 435/325; 435/252.3; 435/254.11; 536/23.1; 536/23.5; 536/24.3; 536/23.4; 530/351
(58) Field of Search ................................. 435/69.5, 69.7, 435/6, 70.1, 71.1, 71.2, 172.3, 325, 252.3, 254.11, 471; 536/23.1, 23.4, 23.5, 24.3, 24.31; 530/351

(56) References Cited

U.S. PATENT DOCUMENTS

| 5,459,128 | 10/1995 | Rollins et al. | 514/8 |
| 5,504,003 | 4/1996 | Li et al. | 435/240.2 |
| 5,571,713 | 11/1996 | Lyle et al. | 435/240.2 |

FOREIGN PATENT DOCUMENTS 0488900 6/1992 (EP).

OTHER PUBLICATIONS

Bartels, J. et al., "Human Dermal Fibroblasts Express Eotaxin: Molecular Cloning, mRNA Expression, and Identification of Eotaxin Sequence Variants," *Biochemical and Biophysical Research Communications*, vol. 225, 1045–1051 (1996).
Fan, X. et al., "Molecular Cloning of a Gene Selectively Induced by Gamma Interferon from Human Macrophage Cell Line U937," *Molecular and Cellular Biology*, vol. 9, No. 5, 1922–1928 (1989).
Furutani, Y. et al., "Cloning and Sequencing of the cDNA for Human Monocyte Chemotactic and Activating Factor (MCAF)," *Biochemical and Biophysical Research Communications*, vol. 159, No. 1, 249–255 (1989).
Garcia–Zepeda, E. et al., "Human Eotaxin is a Specific Chemoattractant for Eosinophil Cells and Provides a New Mechanism to Explain Tissue Eosinophilia," *Nature Medicine*, vol. 2, No. 4, 449–456 (1996).

Kumar et al. GenBank™ Accession No. U29653 for, "Canis Familaris Monocyte Chemoattractant Protein–1 mRNA, Complete cds;" Jan. 2, 1997.
Schwarz E. GenBank™ Accession No. X60001 for, "H. Sapiens Gene for JE Protein, Exons 3 and 4;" Nov. 3, 1992.
Williams et al GenBank™ Accession No. Y08358 for, "R. Norvegicus mRNA for Eotaxin;" Dec. 2, 1996.
Werner F GenBank™ Accession No. Z12297 for, "M. Musculus mRNA for Intercrine;" Dec. 22, 1993.
Heinrich, J. et al., "The Product of a Novel Growth Factor–Activated Gen, fic, is a Biologically Active "C–C" –Type Cytokine," *Molecular and Cellular Biology*, vol. 13, No. 4, 2020–2030 (1993).
Hosang, K. et al., "Porcine Luteal Cells Express Monocyte Chemoattractant Protein–1 (MCP–1): Analysis by Polymerase Chain Reaction and cDNA Cloning," *Biochemical and Biophysical Research Communications*, vol. 199, No. 2, 962–968 (1994).
Hosang, K. et al., "Porcine Luteal Cells Express Monocyte Chemoattractant Protein–2 (MCP–2): Analysis by cDNA Cloning and Northern Analysis," *Biochemical and Biophysical Research Communications*, vol. 205, No. 1, 148–153 (1994).
Jia, G. et al., "Distinct Expression and Function of the Novel Mouse Chemokine Monocyte Chemotactic Protein–5 in Lung Allergic Inflammation," *J. Exp. Med.*, vol. 184, 1939–1951 (1996).
Jose, P.J. et al., "Eotaxin: A Potent Eosinophil Chemoattractant Cytokine Detected in a Guinea Pig Model of Allergic Airways Inflammation," *J. Exp. Med.*, vol. 179, 881–887 (1994).
Jose, P.J. et al., "Eotaxin: Cloning of an Eosinophil Chemoattractant Cytokine and Increased mRNA Expression in Allergen–Challenged Guinea–Pig Lungs," *Biochemical and Biophysical Research Communications*, vol. 205, No. 1, 788–794 (1994).
Kawahara, R. and Deuel, T., "Platelet–derived Growth Factor–inducible Gene JE is a Member of a Family of Small Inducible Genes Related to Platelet Factor 4," *The Journal of Biological Chemistry*, vol. 264, No. 2, 679–682 (1989).
Kitaura, M. et al., "Molecular Cloning of Human Eotaxin, an Eosinophil–selective CC Chemokine, and Identification of a Specific Eosinophil Eotaxin Receptor, CC Chemokine Receptor 3," *The Journal of Biological Chemistry*, vol. 271, No. 13, 7725–7730 (1996).
Kulmburg, P. et al., "Immunoglobulin E Plus Antigen Challenge Induces a Novel Intercrine/Chemokine in Mouse Mast Cells," *J. Exp. Med.*, vol. 176, 1773–1778 (1992).

(List continued on next page.)

*Primary Examiner*—Prema Mertz
(74) *Attorney, Agent, or Firm*—Lahive & Cockfield, LLP; Amy E. Mandragouras; Maria C. Laccotripe

(57) ABSTRACT

The present invention relates to the discovery of novel genes encoding Monocyte Chemotactic Protein-5 (MCP-5) polypeptides. Therapeutics, diagnostics and screening assays based on these molecules are also disclosed.

23 Claims, 4 Drawing Sheets

OTHER PUBLICATIONS

Figure 2A:
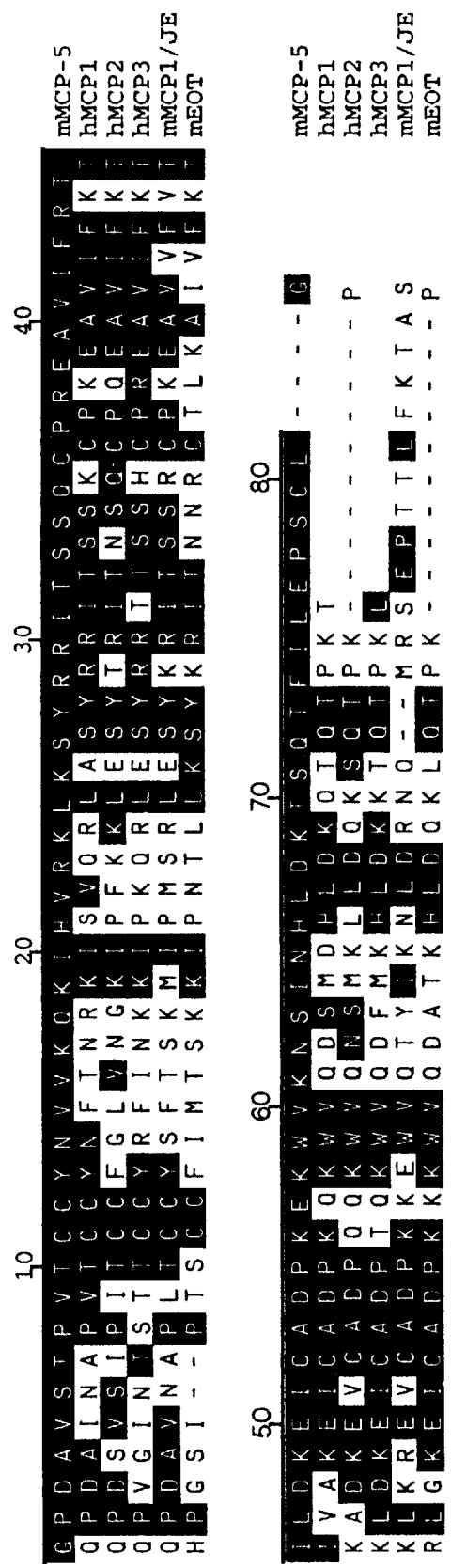

Li, Y. et al., "The Expression of Monocyte Chemotactic Protein (MCP–1) in Human Vascular Endothelium in vitro and in vivo," *Molecular and Cellular Biochemistry*, vol. 126, 61–68 (1993).

Opdenakker, G. et al., "Human Monocyte Chemotactic Protein–3 (MCP–3): Molecular Cloning of the cDNA and Comparison with Other Chemokines," *Biochemical and Biophysical Research Communications*, vol. 191, No. 2, 535–542 (1993).

Opdenakker, G. et al., "The Human MCP–3 Gene (SCYA7): Cloning, Sequence Analysis, and Assignment to the C–C Chemokine Gene Cluster on Chromosome 17q11.2–q12," *Genomics*, vol. 21, 403–408 (1994).

Ponath, P. et al., "Cloning of the Human Eosinophil Chemoattractant, Eotaxin," *J. Clin. Invest.*, vol. 97, No. 3, 604–612 (1996).

Rollings, B. et al., "The Human Homolog of the JE Gene Encodes a Monocyte Secretory Protein," *Molecular and Cellular Biology*, vol. 9, No. 11, 4687–4695 (1989).

Rothenberg, M. et al., "Constitutive and Allergen–induced Expression of Exotaxin mRNA in the Guinea Pig Lung," *J. Exp. Med.*, vol. 181, 1211–1216 (1995).

Shyy, Y. et al., "Structure of Human Monocyte Chemotactic Protein Gene and its Regulation by TPA," *Biochemical and Biophysical Research Communications*, vol. 169, No. 2, 346–351 (1990).

Thirion, S. et al., "Mouse Macrophage Derived Monocyte Chemotactic Protein–3: cDNA Cloning and Identification as MARC/FIC," *Biochemical and Biophysical Research Communications*, vol. 201, No. 2, 493–499 (1994).

Wempe, F. et al., "Cloning of the Gene for Bovine Monocyte Chemoattractant Protein–2," *DNA and Cell Biology*, vol. 13, No. 1, 1–8 (1994).

Yoshimura, T., "cDNA Cloning of Guinea Pig Monocyte Chemoattractant Protein–1 and Expression of the Recombinant Protein." *The Journal of Immunology*, vol. 150, No. 11, 5025–5032 (1993).

Yoshimura, T. and Leonard, E., "Human Monocyte Chemoattractant Protein–1 (MCP–1)," *Chemotactic Cytokines*, 47–56 (1991).

Yoshimura, T. and Yuhki, N., "Neutrophil Attractant/Activation Protein–1 and Monocyte Chemoattractant Protein–1 Rabbit," *The Journal of Immunology*, vol. 146, No. 10, 3483–3488 (1991).

Yoshimura, T. et al., "Human Monocyte Chemoattractant Protein–1 (MCP–1)," *FEBS Letters*, vol. 244, No. 2, 487–493 (1989).

Yoshimura, T. et al., "Molecular Cloning of Rat Monocyte Chemoattractant Protein–1 (MCP–1) and its Expression in Rat Spleen Cells and Tumor Cell Lines," *Biochemical and Biophysical Research Communications*, vol. 174, No. 2, 504–509 (1991).

Zach, O. et al., "Sequence of the Porcine Full–length cDNA Encoding Ribosomal Protein rpS12," *Gene*, vol. 159, 277–278 (1995).

Sambrook et al. (1989) Molecular cloning A Laboratory Manual Cold Spring Harbor Laboratory Press pp. 17.2–17.10.*

Stratagene Catalog (1988) p. 39.*

Keller & Manak (1993) DNA Probes Background, Applications Procedures, Stockton Press, pp. 173–198.*

Cunningham et al. (1989) Science vol. 244, pp. 1081–1085.*

George et al. (1988) Macromolecular Sequencing & Synthesis, Alan R. Liss, N.Y., pp. 127–149.*

* cited by examiner

FIG. 1

```
                                                                              M   K   I   S   T   L     6
AGAGACACTGGTTCCTGACTCCCTCTAGCTTTCATTTGAAGTCTTTGACCCTCAAC ATG AAG ATT TCC ACA CTT    73

L   C   L   L   L   I   A   T   T   I   S   P   Q   V   L   A   G   P   D   A     26
CTA TGC CTC CTG CTC ATA GCT ACC ACC ATC AGT CCT CAG GTA TTG GCT GGA CCA GAT GCG   133

V   S   T   P   V   T   C   C   Y   N   V   V   K   Q   K   I   H   V   R   K     46
GTG AGC ACC CCA GTC ACG TGC TGT TAT AAT GTT GTT AAG CAG AAG ATT CAC GTC CGG AAG   193

L   K   S   Y   R   R   I   T   S   Q   C   P   R   E   A   V   I   F   R         66
CTG AAG AGC TAC AGG AGA ATC ACA AGC CAG TGT CCC CGG GAA GCT GTG ATC TTC AGG       253

T   I   L   D   K   E   I   C   A   D   P   K   E   K   W   V   K   N   S   I     86
ACC ATA CTG GAT AAG GAG ATC TGT GCT GAC CCC AAG GAG AAG TGG GTT AAG AAT TCC ATA   313

N   H   L   D   K   T   S   Q   T   F   I   L   E   P   S   C   L   G   *        105
AAC CAC TTG GAT AAG ACG TCT CAA ACC TTC ATC CTT GAA CCT TCA TGT CTA GGC TGA       370

GAGTTCCAAAAACTCTTACGTATTCCCCCTGAAGTTCCCCACGGGCAGGGTGATATTTATTATGATATCTAAAAAGAG    449

ATGTTTTTAATAATTTAAACAAACTTGCTTAATAATATTTAAGTAATGGTATTTAAGTAATAATATTTGGGCCAATTAATCCGAA    528

TCTAATTTAAAA    540
```

Reduction of OVA-induced lung eosinophil infiltration by anti-mMCP-5 blockade *in vivo*

NUCLEIC ACID MOLECULES ENCODING MONOCYTE CHEMOTACTIC PROTEIN 5 (MCP-5) MOLECULES AND USES THEREFOR

CROSS-REFERENCE TO RELATED APPLICATION

This application claims the benefit under 35USC 119(e) of Ser. No. 60/026,882 filed Sep. 18, 1996.

1. BACKGROUND OF THE INVENTION

Chemokines are proteins involved in the activation of chemotaxis of leukocytes. They are believed to be important mediators of inflammation. (Baggiolini et al., *Immunology Today* 15:127, 1994).

Chemokines have been divided into three families. In chemokines of the C-X-C family, one amino acid separates the first two cysteines. Chemokines in this family are thought to be involved in the chemotaxis of neutrophils, induction of changes in cell shape, transient increase of intracellular calcium, granule exocytosis, and respiratory burst. Interleukin-8 (IL-8), neutrophil activating protein-2 (NAP-2) and granulocyte chemotactic protein (GCP) belong to this class. All known CXC chemokines have been mapped to human chromosome 4 and mouse chromosome 5.

In the C-C family, the first two cysteines are adjacent to one another. Members of this family are chemotactic for monocytes, but not neutrophils. Recent studies have shown that they are capable of activating basophils and eosinphils. Proteins belonging to the C-C class of chemokines include monocyte chemotactic proteins 1, 2, and 3 (MCP-1, MCP-2, and MCP-3), RANTES, and macrophage inflammatory proteins α and β (MIP-1α and MIP-1β). Recently, MIP-3, MIP-4, and MIP-1γ have also been described (WO 95/17092). All known C-C chemokines have been mapped to human chromosome 17 and mouse chromosome 11.

An example of a third class of chemokine has also been identified. This chemokine, lymphotactin, was isolated from progenitor T lymphocytes. Lymphotactin is chemotactic to lymphocytes (Kelner et al., *Science* 266:1395, 1994).

Unlike the chemokines of the CC and CXC families in which two disulfide bonds stabilize the protein, lymphotactin has only one disulfide bond. Lymphotactin was mapped to human and mouse chromosome 1.

A variety of cell types are involved in the various inflammatory states. For example, acute infiltrates found after bacterial infection are mainly neutrophilic, while mononuclear cells predominate after infection by an intracellular pathogen. Basophils and easinophils dominate in both immediate-type allergic response and autoimmune diseases. Increased understanding of the regulation of these various cell types by chemokines will facilitate the development of more effective therapies for disorders related to inflammation.

2. SUMMARY OF THE INVENTION

The present invention is based, at least in part, on the discovery of novel C-C chemokine molecules, referred to herein as "Monocyte Chemotactic Protein 5" (MCP-5) nucleic acid and polypeptide molecules. An exemplary MCP-5 molecule has been deposited with the American Type Culture Collection (ATCC)® on Sep. 19, 1996 and has been assigned ATCC® designation number 98172. The murine MCP-5 gene transcript is approximately 540 base pairs in length, including 5' and 3' untranslated regions and a 341 base open reading frame encoding a 104 amino acid polypeptide. The mature protein (minus the 22 amino acid signal sequence) is comprised of about 82 amino acids, containing 5 cysteine residues, four of which create the characteristic motif of the CC chemokine family. MCP-5 is mainly expressed by alveolar macrophages and smooth muscle cells of the eosinophilic lung. The presence of lymphocytes was found to be critical for its expression during allergic inflammation. During non-inflammatory situations, expression of MCP-5 in the lymph nodes and thymus is constitutive and restricted to stromal clls (macrophages and dendritic cells) present in the germinal centers of the lymphoid follicles. The murine MCP-5 polypeptide is approximately 11–12 kD.

In one aspect, the invention features isolated vertebrate MCP-5 nucleic acid molecules. The disclosed molecules can be non-coding, (e.g. probe, antisense or ribozyme molecules) or can encode a functional MCP-5 polypeptide (e.g. a polypeptide which specifically modulates, e.g., by acting as either an agonist or antagonist, at least one bioactivity of the human MCP-5 polypeptide). In one embodiment, the nucleic acid molecules can hybridize to the MCP-5 gene contained in ATCC® designation number 98172 or to the complement of the MCP-5 gene contained in ATCC® designation number 98172. In another embodiment, the nucleic acids of the present invention can hybridize to a vertebrate MCP-5 gene or to the complement of a vertebrate MCP-5 gene. In a further embodiment, the claimed nucleic acid can hybridize with the nucleic acid sequence shown in FIG. 1 (SEQ ID NOs. 1 and 3). In a preferred embodiment, the hybridization is conducted under mildly stringent or stringent conditions.

In further embodiments, the nucleic acid molecule is a MCP-5 nucleic acid that is at least 70%, preferably 80%, more preferably 85%, and even more preferably at least 90% or 95% homologous in sequence to any of the nucleic acids shown as SEQ ID Nos: 1 or 3 or to the complement of the nucleic acid shown as SEQ ID Nos: 1 or 3. In a further embodiment, the nucleic acid molecule is a MCP-5 nucleic acid that is at least 70%, preferably 80%, more preferably 85% and even more preferably at least 90% or 95% similar in sequence to the MCP-5 gene contained in ATCC® designation number 98172 or to the complement of the MCP-5 gene contained in ATCC® designation number 98172.

The invention also provides probes and primers comprising substantially purified oligonucleotides, which correspond to a region of nucleotide sequence which hybridizes to at least 6 consecutive nucleotides of any of the sequences set forth as SEQ ID Nos: 1 or 3 or complements of any of the sequences set forth as SEQ ID Nos 1 or 3 or naturally occurring mutants thereof. In preferred embodiments, the probe/primer further includes a label group attached thereto, which is capable of being detected.

For expression, the subject nucleic acids can include a transcriptional regulatory sequence, e.g. at least one of a transcriptional promoter (e.g., for constitutive expression or inducible expression) or transcriptional enhancer sequence, which regulatory sequence is operably linked to the gene sequence. Such regulatory sequences in conjunction with a MCP-5 nucleic acid molecule can provide a usefuil vector for gene expression. This invention also describes host cells transfected with said expression vector whether prokaryotic or eukaryotic and in vitro (e.g. cell culture) and in vivo (e.g. transgenic) methods for producing MCP-5 proteins by employing said expression vectors.

In another aspect, the invention features isolated MCP-5 polypeptides, preferably substantially pure preparations, e.g.

of plasma purified or recombinantly produced polypeptides. In a preferred embodiment, the polypeptide is approximately 11 kD. In particularly preferred embodiments, the subject polypeptides have a MCP-5 bioactivity, for example, they are capable of inducing eosinophil; monocyte- and lymphocyte- (e.g. B-lymphocyte) mediated inflammation.

In a preferred embodiment, the MCP-5 polypeptide is encoded by a nucleic acid which hybridizes with the nucleic acid sequences represented in SEQ ID Nos. 1 or 3 or with the gene or gene fragment contained in ATCC® Designation No. 98172. In a further preferred embodiment, the MCP-5 polypeptide is comprised of the amino acid sequence set forth in SEQ ID No. 2. The subject MCP-5 proteins also include modified proteins, which are resistant to post-translational modification, as for example, due to mutations which alter modification sites (such as tyrosine, threonine, serine or aspargine residues), or which prevent glycosylation of the protein, or which prevent interaction of the protein with intracellular proteins involved in signal transduction.

The MCP-5 polypeptides can comprise a full length protein or they can comprise a fragment corresponding to one or more particular motifs/domains, or to arbitrary sizes, e.g., at least 5, 10, 25, 50, 100, 150 or 200 amino acids in length. In preferred embodiments, the polypeptide is capable of inducing eosinophil-, monocyte- and lymphocyte- (e.g., B-lymphocyte) mediated inflammation.

Another aspect of the invention features chimeric molecules (e.g., fusion proteins) comprised of a MCP-5 protein. For instance, the MCP-5 protein can be provided as a recombinant fusion protein which includes a second polypeptide portion, e.g., a second polypeptide having an amino acid sequence unrelated (heterologous) to the MCP-5 polypeptide.

Yet another aspect of the present invention concerns an immunogen comprising a MCP-5 polypeptide in an immunogenic preparation, the immunogen being capable of eliciting an immune response specific for a MCP-5 polypeptide; e.g. a humoral response, an antibody response and/or cellular response. In a preferred embodiment, the immunogen comprises an antigenic determinant, e.g. a unique determinant of a protein encoded by the nucleic acids set forth in SEQ ID Nos. 1 or 3; or as set forth in SEQ ID NO.2.

A still further aspect of the present invention features antibodies and antibody preparations specifically reactive with an epitope of a MCP-5 protein. The instant disclosed antibodies are useful in down modulating (e.g. inhibiting or suppressing or down regulating) an eosinophil, monocyte- and lymphocyte- (e.g. B-lymphocyte) mediated inflammation.

A still flrther aspect of the present invention features methods of therapy based on modulating The invention also features transgenic non-human animals which include (and preferably express) a heterologous form of a MCP-5 gene described herein, or which misexpress an endogenous MCP-5 gene (e.g., an animal in which expression of one or more of the subject MCP-5 proteins is disrupted). Such transgenic animals can serve as animal models for studying cellular and tissue disorders comprising mutated or mis-expressed MCP-5 alleles or for use in drug screening. Alternatively, such transgenic animals can be usefuil for expressing recombinant MCP-5 polypeptides.

A further aspect of the present invention provides methods of determining if a subject is at risk for a disorder characterized by inappropriate (e.g., too high, too low) MCP-5 protein expression, such as, for example, allergic inflammation of tissues, such as epithelia . The method includes detecting, in a tissue of the subject, the presence or absence of a genetic lesion characterized by at least one of (i) a mutation of a gene encoding a MCP-5 protein, e.g. represented in SEQ ID No: 1 or 3 or a homolog thereof; (ii) the mis-expression of a MCP-5 gene or (iii) an error or mutation in the promoter that may lead to aberrant expression. In preferred embodiments, detecting the genetic lesion includes ascertaining the existence of at least one of: a deletion of one or more nucleotides from a MCP-5 gene; an addition of one or more nucleotides to the gene; a substitution of one or more nucleotides of the gene; a gross chromosomal rearrangement of the gene; an alteration in the level of a messenger RNA transcript of the gene; the presence of a non-wild type splicing pattern of a messenger RNA transcript of the gene; a non-wild type level of the protein; and/or an aberrant level of soluble MCP-5 protein.

For example, detecting the genetic lesion can include (i) providing a probe/primer comprised of an oligonucleotide which hybridizes to a sense or antisense sequence of a MCP-5 gene or naturally occurring mutants thereof, or 5' or 3' flanking sequences naturally associated with the MCP-5 gene; (ii) contacting the probe/primer to an appropriate nucleic acid containing sample; and (iii) detecting, by hybridization of the probe/primer to the nucleic acid, the presence or absence of the genetic lesion; e.g. wherein detecting the lesion comprises utilizing the probe/primer to determine the nucleotide sequence of the MCP-5 gene and, optionally, of the flanking nucleic acid sequences. For instance, the primer can be employed in a polymerase chain reaction (PCR) or in a ligation chain reaction (LCR). In alternate embodiments, the level of a MCP-5 protein is detected in an immunoassay using an antibody which is specifically immunoreactive with the MCP-5 protein.

Other features and advantages of the invention will be apparent from the following detailed description and claims.

3. BRIEF DESCRIPTION OF THE FIGURES

FIG. 1 shows a DNA sequence of the murine MCP-5 gene including 5' and 3' noncoding sequences and coding sequences (SEQ ID NOs. 1 and 3), as well as the deduced amino acid sequence of the MCP-5 protein (SEQ ID NO 2).

FIG. 2 shows a comparison of the amino acid sequence of mMCP-5 mature peptide with that of human and mouse C-C chemokines and the phylogenetic tree of human and mouse members of the C-C chemokine family including mMCP-5. (A) Amino acid sequence alignment of mMCP-5 with other human and mouse CC chemokines. (B) Phylogenetic tree of CC chemokine family including mMCP-5 (bold). Distances to branch points are proportional to aminoacid sequence divergence from predicted ancestral sequences. The Clustal alignment method grouped mMCP-5 with hMCP-1 and hMCP-3. Names of CC chemokine genes are shown to the right end of the tree. Percent similarity between the nucleotide sequence of the coding region or the amino acid sequence of the mature peptide of mMCP-5 and those of other human and mouse CC chemokines are shown at right in the figure.

Figure 3A:
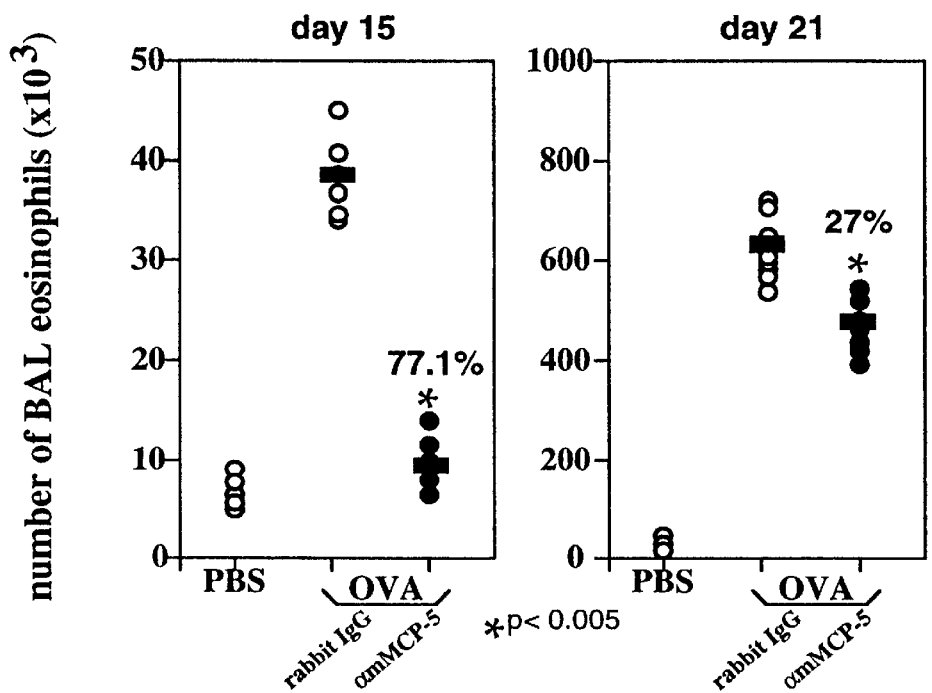
Figure 3B:
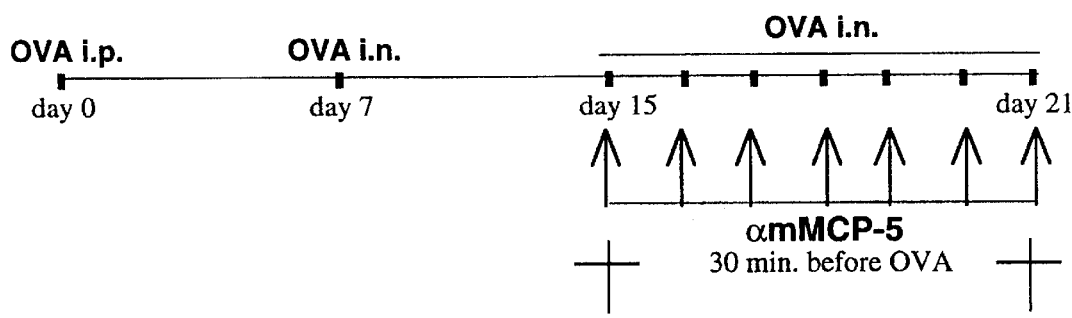

FIG. 3 shows the blocking of mMCP-5 protein with specific neutralizing antibodies during the course of OVA-induced allergic inflammation.

4. DETAILED DESCRIPTION OF THE INVENTION 4.1. General

The present invention is based on the discovery of novel chemokine genes, referred to herein as "Monocyte Chemotactic Protein-5" or "MCP-5" genes, that are chemotactic for eosinophils, monocytes and lymphocytes cloned from the eosinophilic lung. Studies on the expression and function of MCP-5 in a model of lung allergic inflammation revealed that its mRNA expression in vivo is regulated differently from that of other C-C chemokines. During lung allergic inflammation, MCP-5 is mainly produced by macrophages, but the presence of lymphocytes is essential for its expression in vivo. Also it was found that MCP-5 can either enhance or reduce the chemotaxis of eosinophils to Eotaxin in a concentration dependent manner. Therefore MCP-5 is likely to play a pivotal role during lung allergic inflammation.

MCP-5 was found to be constitutively expressed in lymph nodes and thymus. In the lymph node it is expressed exclusively by stromal cells (macrophages and/or follicular dendritic cells) present in the germinal centers of the lymphoid follicles and demonstrated its ability to attract B lymphocytes. MCP-5 presumably mediates recruitment of B lymphocytes to the B-cell areas of the lymphoid follicles during the formation of the germinal center. It appears that MCP-5 expression can be either inducible (allergic inflammation) or constitutive (lymph nodes). In these two situations, its expression possibly results in either the recruitment of inflammatory leukocytes to the lung or in the directed migration of B- lymphocytes to the germinal center.

MCP-5 induces chemotactic transmigration of monocytes, lymphocytes and eosinophils, but not neutrophils.

The MCP-5 gene DNA, which was deposited with the American Type Culture Collection (ATCC)® on Sep. 19, 1996 and has been assigned ATCC designation number 98172, is approximately 540 base pairs in length including 5' and 3' untranslated regions and a 341 base pair coding sequence. The gene is constitutively expressed in the lymph nodes and thymus and is inducibly expressed in allergic inflammation tissue (e.g., lung). The MCP-5 gene encodes a polypeptide of approximately 11–12 kD.

Accordingly, certain aspects of the present invention relate to nucleic acid molecules encoding MCP-5 proteins, antisense molecules, ribozymes and triplex molecules that block expression of MCP-5 genes, MCP-5 proteins, antibodies immunoreactive with MCP-5 proteins, and preparations of such compositions. In addition, the present invention relates to therapies, which are based on upmodulating (e.g., stimulating) or dowmnodulating (e.g., inhibiting or suppressing) MCP-5 genes and proteins. Moreover, the present invention provides diagnostic assays and reagents for detecting and treating disorders involving, for example, aberrant expression (or loss thereof) of MCP-5 genes. Other aspects of the invention are described below or will be apparent to those skilled in the art in light of the present disclosure.

4.2 Definitions

For convenience, the meaning of certain terms and phrases employed in the specification, examples, and appended claims are provided below.

An "allergen" refers to a substance that can induce an allergic or asthmatic response in a susceptible subject. The list of allergens is enormous and can include pollens, insect venoms, animal dander dust, fungal spores and drugs (e.g. penicillin). Examples of natural, animal and plant allergens include proteins specific to the following genuses: Canine (*Canis familiaris*); Dermatophagoides (e.g. *Dermatophagoides farinae*); Felis (*Felis domesticus*); Ambrosia (*Ambrosia artemiisfolia*; Lolium (e.g. *Lolium perenne* or *Lolium multiflorum*); Cryptomeria (*Cryptomeria japonica*); Alternaria (*Alternaria alternata*); Alder; Alnus (*Alnus gultinosa*); Betula (*Betula verrucosa*); Quercus (*Quercus alba*); Olea (*Olea europa*); Artemisia (*Artemisia vulgaris*); Plantago (e.g. *Plantago lanceolata*); Parietaria (e.g. *Parietaria officinalis* or *Parietaria judaica*); Blattella (e.g. *Blattella germanica*); Apis (e.g. *Apis multiflorum*); Cupressus (e.g. *Cupressus sempervirens, Cupressus arizonica* and *Cupressus macrocarpa*); Juniperus (e.g. *Juniperus sabinoides, Juniperus virginiana, Juniperus communis* and *Juniperus ashei*); Thuya (e.g. *Thuya orientalis*); Chamaecyparis (e.g. *Chamaecyparis obtusa*); Periplaneta (e.g. *Periplaneta americana*); Agropyron (e.g. *Agropyron repens*); Secale (e.g. *Secale cereale*); Triticum (e.g. *Triticum aestivum*); Dactylis (e.g. *Dacoydis glomerata*); Festuca (e.g. *Festuca elatior*); Poa (e.g. *Poapratensis* or *Poa compressa*); Avena (e.g. *Avena sativa*); Holcus (e.g. *Holcus lanatus*); Anthoxanthum (e.g. *Anthoxanthum odoratum*); Arrhenatherum (e.g. *Arrhenatherum elatius*); Agrostis (e.g. *Agrostis alba*); Phleum (e.g. *Phleum pratense*); Phalaris (e.g. *Phalaris arundinacea*); Paspalum (e.g. *Paspalum notatum*); Sorghum (e.g. *Sorghum halepensis*); and Bromus (e.g. *Bromus inermis*).

An "allergy" refers to acquired hypersensitivity to a substance (allergen). Allergic conditions include eczema, allergic rhinitis or coryza, hay fever, bronchial asthma, urticaria (hives) and food allergies, and other atopic conditions.

"Asthma"—refers to a disorder of the respiratory system characterized by inflammation, narrowing of the airways and increased reactivity of the airways to inhaled agents. Asthma is frequently, although not exclusively associated with atopic or allergic symptoms.

"Bioactivity" as used herein is meant to include chemotactic activity for immune cells which does not include neutrophils. An MCP-5 bioactivity can also be assessed by the ability to compete with MCP-5 in the ability to promote chemotaxis.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject MCP-5 polypeptides with a second amino acid sequence defining a domain (e.g., polypeptide portion) foreign to and not substantially homologous with any domain of one of the MCP-5 polypeptides. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-MCP-5-Y, wherein MCP-5 represents a portion of the protein which is derived from one of the MCP-5 proteins, and X and Y are independently absent or represent amino acid sequences which are not related to one of the MCP-5 amino acid sequences in an organism, including naturally occurring mutants.

"Complementary" sequences as used herein refer to sequences which have sufficient complementarity to be able to hybridize, forming a stable duplex.

A "delivery complex" shall mean a targeting means (e.g., a molecule that results in higher affinity binding of a gene, protein, polypeptide or peptide to a target cell surface and/or increased cellular uptake by a target cell). Examples of targeting means include: sterols (e.g., cholesterol), lipids (e.g., a cationic lipid, virosome or liposome), viruses (e.g., adenovirus, adeno-associated virus, and retrovirus) or target cell specific binding agents (e.g., ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a MCP-5 polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

As used herein, the term "gene" or "recombinant gene" refers to a nucleic acid molecule comprising an open reading frame encoding one of the MCP-5 polypeptides of the present invention, including both exon and (optionally) intron sequences. A "recombinant gene" refers to nucleic acid molecule encoding a MCP-5 polypeptide and comprising MCP-5 protein-encoding exon sequences, though it may optionally include intron sequences which are either derived from a chromosomal MCP-5 gene or from an unrelated chromosomal gene. Exemplary recombinant genes encoding the subject MCP-5 polypeptides are represented in the appended Sequence Listing. The term "intron" refers to a DNA sequence present in a given gene which is not translated into protein and is generally found between exons.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a fumction of the number of matching or homologous positions shared by the sequences. An "unrelated" or "non-homologous" sequence shares less than 40% identity, though preferably less than 25% identity, with one of the MCP-5 sequences of the present invention.

As used herein, an "immune system deficiency" shall mean a disease or disorder in which the subject's immune system is not flnctioning in normal capacity or in which it would be useful to boost a subject's immune response for example to eliminate a tumor or cancer (e.g. tumors of the brain, lung (e.g. small cell and non-small cell), ovary, breast, prostate, colon, as well as other carcinomas and sarcomas) or an infection in a subject. As described above, MCP-5 agonists are useful for treating immune system deficiencies.

Examples of infectious virus include: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses'); Poxviridae (variola viruses, vaccinia viruses, pox viruses); and Jridoviridae (e.g., African swine fever virus); and unclassified viruses (e.g., the etiological agents of Spongiform encephalopathies, the agent of delta hepatities (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Helicobacter pyloris, Borelia burgdorferi, Legionella pneumophilia*, Mycobacteria sps (e.g. *M. tuberculosis, M avium, M. intracellulare, M. kansaii, M. gordonae), Staphylococcus aureus, Neisseria gonorrhoeae, Neisseria meningitidis, Listeria monocytogenes, Streptococcus pyogenes* (Group A Streptococcus), *Streptococcus agalactiae* (Group B Streptococcus), Streptococcus (viridans group), *Streptococcus faecalis, Streptococcus bovis*, Streptococcus (anaerobic sps.), *Streptococcus pneumoniae*, pathogenic Campylobacter sp., Enterococcus sp., *Haemophilus influenzae, Bacillus antracis, corynebacterium diphtheriae, corynebacterium sp., Erysipelothrix rhusiopathiae, Clostridium perfringers, Clostridium tetani, Enterobacter aerogenes, Klebsiella pneumoniae, Pasturella multocida*, Bacteroides sp., *Fusobacterium nucleatum, Streptobacillus moniliformis, Treponema pallidium, Treponema pertenue*, Leptospira, and *Actinomyces israelli.*

Examples of infectious fungi include: *Cryptococcus neoformans, Histoplasma capsulatum, Coccidioides immitis, Blastomyces dermatitidis, Chlamydia trachomatis, Candida albicans.* Other infectious organisms (i.e., protists) include: *Plasmodium falciparum* and *Toxoplasma gondii.*

The term "interact" as used herein is meant to include detectable interactions between molecules, such as can be detected using, for example, a yeast two hybrid assay. The term interact is also meant to include "binding" interactions between molecules. Interactions may be protein-protein or protein-nucleic acid in nature.

The term "isolated" as used herein with respect to nucleic acids, such as DNA or RNA, refers to molecules separated from other DNAs or RNAs, respectively, that are present in the natural source of the macromolecule. For example, an isolated nucleic acid encoding one of the subject MCP-5 polypeptides preferably includes no more than 10 kilobases (kb) of nucleic acid sequence which naturally immediately flanks the MCP-5 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

"Modulation" as used herein is meant to encompass regulation (e.g., stimulation or activation) or down regulation (e.g., inhibition or suppression) of the expression and/or bioactivity of MCP-5. Agents which upregulate expression make a qualitative change in the amount of MCP-5 produced by a cell while agents which upregulate the bioactivity of MCP-5 make a qualitative change in the ability of MCP-5 to perform a bioactivity. Modulating agents of the present invention can be nucleic acids, polypeptides, antibodies, or compounds. Compounds of the present invention can alter the transcription of bioactivity of MCP-5, such as by altering the synthesis or degrelation rate of MCP-5.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse. The term "chimeric animal" is used herein to refer to animals in which the recombinant gene is found, or in which the recombinant is expressed in some but not all cells of the animal. The term "tissue-specific chimeric animal" indicates that one of the recombinant MCP-5 genes is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g., cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangably herein when referring to a gene product.

The term "recombinant protein" refers to a polypeptide of the present invention which is produced by recombinant DNA techniques, wherein generally, DNA encoding a MCP-5 polypeptide is inserted into a suitable expression vector which is in turn used to transform a host cell to produce the heterologous protein. Moreover, the phrase "derived from", with respect to a recombinant MCP-5 gene, is meant to include within the meaning of "recombinant protein" those proteins having an amino acid sequence of a native MCP-5 protein, or an amino acid sequence similar thereto which is generated by mutations including substitutions and deletions (including truncation) of a naturally occurring form of the protein.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400 or 425 consecutive nucleotides of a vertebrate, preferably mammalian, MCP-5 gene, such as the MCP-5 sequence designated in SEQ ID Nos: 1 or 3, or a sequence complementary thereto, or naturally occurring mutants thereof, such that it shows more than 10 times more hybridization, preferably more than 100 times more hybridization, and even more preferably more than 100 times more hybridization than it does to a cellular nucleic acid (e.g., mRNA or genomic DNA) encoding a protein other than a vertebrate, preferably mammalian, MCP-5 protein as defined herein.

"Transcriptional regulatory sequence" is a generic term used throughout the specification to refer to DNA sequences, such as initiation signals, enhancers, and promoters, which induce or control transcription of protein coding sequences with which they are operably linked. in preferred embodiments, transcription of one of the recombinant MCP-5 genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of MCP-5 proteins.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a MCP-5 polypeptide or, in the case of anti-sense expression from the transferred gene, the expression of a naturally-occurring form of the MCP-5 protein is disrupted.

As used herein, the term "transgene" means a nucleic acid sequence encoding, e.g., one of the MCP-5 polypeptides, or an antisense transcript thereto, which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, (e.g., as intron), that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the MCP-5 proteins, e.g., either agonistic or antagonistic forms. However, transgenic animals in which the recombinant MCP-5 gene is silent are also contemplated, as for example, the FLP or CRE recombinase dependent constructs described below. Moreover, "transgenic animal" also includes those recombinant animals in which gene disruption of one or more MCP-5 genes is caused by human intervention, including both recombination and antisense techniques.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

4.3 Nucleic Acids of the Present Invention

As described below, one aspect of the invention pertains to isolated nucleic acids comprising nucleotide sequences encoding MCP-5 polypeptides, and/or equivalents of such nucleic acids. The term equivalent is understood to include nucleotide sequences encoding finctionally equivalent MCP-5 polypeptides or functionally equivalent peptides having an activity of a MCP-5 protein such as described herein. Equivalent nucleotide sequences will include sequences that differ by one or more nucleotide substitution, addition or deletion, such as allelic variants; and will, therefore, include sequences that differ from the nucleotide sequence of the MCP-5 gene shown in SEQ ID Nos: 1 or 3 due to the degeneracy of the genetic code.

Preferred nucleic acids are vertebrate MCP-5 nucleic acids. Particularly preferred vertebrate MCP-5 nucleic acids are mammalian. Regardless of species, particularly preferred MCP-5 nucleic acids encode polypeptides that are at least 80% similar to an amino acid sequence of a vertebrate MCP-5 protein. In one embodiment, the nucleic acid is a cDNA encoding a polypeptide having at least one bioactivity of the subject MCP-5 polypeptide. Preferably, the nucleic acid includes all or a portion of the nucleotide sequence corresponding to the nucleic acid of SEQ ID No 1 or 3.

Still other preferred nucleic acids of the present invention encode a MCP-5 polypeptide which is comprised of at least 2, 5, 10, 25, 50, 100, 150 or 200 amino acid residues. For example, preferred nucleic acid molecules for use as probes/primer or antisense molecules (i.e. noncoding nucleic acid molecules) can comprise at least about 6, 12, 20, 30, 50, 60, 70, 80, 90 or 100 base pairs in length, whereas coding nucleic acid molecules can comprise about 50, 60, 70, 80, 90, or 100 base pairs.

Another aspect of the invention provides a nucleic acid which hybridizes under stringent conditions to a nucleic acid represented by SEQ ID No: 1 or 3. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature of salt concentration may be held constant while the other variable is changed In a preferred embodiment, a MCP-5 nucleic acid of the present invention will bind to one of SEQ ID Nos 1 or 3 under moderately stringent conditions, for example at about 2.0×SSC and about 40° C. In a particularly preferred embodiment, a MCP-5 nucleic acid of the present invention will bind to one of SEQ ID Nos: 1 or 3 under high stringency conditions.

Preferred nucleic acids have a sequence at least 70%, and more preferably 75% homologous and more preferably 80% and even more preferably at least 85% homologous with an amino acid sequence of a MCP-5 gene, e.g., such as a sequence shown in one of SEQ ID Nos: 1 or 3. Nucleic acids at least 90%, more preferably 95%, and most preferably at least about 98–99% homologous with a nucleic sequence represented in one of SEQ ID Nos: 1 or 3 are of course also within the scope of the invention. In preferred embodiments, the nucleic acid is mammalian and in particularly preferred embodiments, includes all or a portion of the nucleotide sequence corresponding to the coding region of one of SEQ ID Nos: 1 or 3.

Nucleic acids having a sequence that differs from the nucleotide sequences shown in one of SEQ ID Nos: 1 or 3 due to degeneracy in the genetic code are also within the scope of the invention. Such nucleic acids encode finctionally equivalent peptides (i.e., a peptide having a biological activity of a MCP-5 polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a MCP-5 polypeptide. However, it is expected that DNA sequence polymorphisms that do lead to changes in the amino acid sequences of the subject MCP-5 polypeptides will exist among mammals. One skilled in the art will appreciate that these variations in one or more nucleotides (e.g., up to about 3–5% of the nucleotides) of the nucleic acids encoding polypeptides having an activity of a MCP-5 polypeptide may exist among individuals of a given species due to natural allelic variation.

As indicated by the examples set out below, MCP-5 protein-encoding nucleic acids can be obtained from mRNA present in any of a number of eukaryotic cells. It should also be possible to obtain nucleic acids encoding MCP-5 polypeptides of the present invention from genomic DNA from both adults and embryos. For example, a gene encoding a MCP-5 protein can be cloned from either a cDNA or a genomic library in accordance with protocols described herein, as well as those generally known to persons skilled in the art. Examples of tissues and/or libraries suitable for isolation of the subject nucleic acids include thymus, lymph nodes and inflammatory tissue. cDNA encoding a MCP-5 protein can be obtained by isolating total mRNA from a cell, e.g., a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a MCP-5 protein can also be cloned using established polymerase chain reaction techniques in accordance with the nucleotide sequence information provided by the invention. The nucleic acid of the invention can be DNA or RNA or analogs thereof. A preferred nucleic acid is a cDNA represented by a sequence selected from the group consisting of SEQ ID Nos: 1 or 3.

4.3.1. Vectors

This invention also provides expression vectors containing a nucleic acid encoding a MCP-5 polypeptide, operably linked to at least one transcriptional regulatory sequence. "Operably linked" is intended to mean that the nucleotide sequence is linked to a regulatory sequence in a manner which allows expression of the nucleotide sequence. Regulatory sequences are art-recognized and are selected to direct expression of the subject MCP-5 proteins. Accordingly, the term "transcriptional regulatory sequence" includes promoters, enhancers and other expression control elements. Such regulatory sequences are described in Goeddel; *Gene Expression Technology: Methods in Enzymology* 185, Academic Press, San Diego, Calif. (1990). In one embodiment, the expression vector includes a recombinant gene encoding a peptide having an agonistic activity of a subject MCP-5 polypeptide, or alternatively, encoding a peptide which is an antagonistic form of the MCP-5 protein. Such expression vectors can be used to transfect cells and thereby produce polypeptides, including fusion proteins, encoded by nucleic acids as described herein. Moreover, the gene constructs of the present invention can also be used as a part of a gene therapy protocol to deliver nucleic acids encoding either an agonistic or antagonistic form of one of the subject MCP-5 proteins. Thus, another aspect of the invention features expression vectors for in vivo or in vitro transfection and expression of a MCP-5 polypeptide in particular cell types so as to reconstitute the function of, or alternatively, abrogate the function of MCP-5-induced signaling in a tissue. This could be desirable, for example, when the naturally-occurring form of the protein is misexpressed; or to deliver a form of the protein which alters differentiation of tissue. Expression vectors may also be employed to inhibit neoplastic transformation.

In addition to viral transfer methods, such as those illustrated above, nonviral methods can also be employed to cause expression of a subject MCP-5 polypeptide in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject MCP-5 polypeptide gene by the targeted cell. Exemplary targeting means of this type include liposomal derived systems, poly-lysine conjugates, and artificial viral envelopes.

4.3.2. Probes and Primers

Moreover, the nucleotide sequences determined from the cloning of MCP-5 genes from mammalian organisms will frrther allow for the generation of probes and primers designed for use in identifying and/or cloning MCP-5 homologs in other cell types, e.g., from other tissues, as well as MCP-5 homologs from other mammalian organisms. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of sense or anti-sense sequence selected from the group consisting of SEQ ID No: 1 or 3 or naturally occurring mutants thereof. For instance, primers based on the nucleic acid represented in SEQ ID Nos:1 or 3 can be used in PCR reactions to clone MCP-5 homologs.

Likewise, probes based on the subject MCP-5 sequences can be used to detect transcripts or genomic sequences encoding the same or homologous proteins. In preferred embodiments, the probe further comprises a label group attached thereto and able to be detected, e.g., the label group is selected from amongst radioisotopes, fluorescent compounds, enzymes, and enzyme co-factors.

As discussed in more detail below, such probes can also be used as a part of a diagnostic test kit for identifying cells or tissue which misexpress a MCP-5 protein, such as by measuring a level of a MCP-5-encoding nucleic acid in a sample of cells from a patient; e.g., detecting MCP-5 mRNA levels or determining whether a genomic MCP-5 gene has been mutated or deleted. Briefly, nucleotide probes can be generated from the subject MCP-5 genes which facilitate histological screening of intact tissue and tissue samples for the presence (or absence) of MCP-5-encoding transcripts. Similar to the diagnostic uses of anti-MCP-5 antibodies, the use of probes directed to MCP-5 messages, or to genomic MCP-5 sequences, can be used for both predictive and therapeutic evaluation of allelic mutations which might be manifest in, for example, a predisposition to inflammation. Used in conjunction with immunoassays as described herein, the oligonucleotide probes can help facilitate the determination of the molecular basis for a disorder which may involve some abnormality associated with expression (or lack thereof) of a MCP-5 protein. For instance, variation in polypeptide synthesis can be differentiated from a mutation in a coding sequence.

4.3.3. Antisense, Ribozyme and Triplex Techniques

Another aspect of the invention relates to the use of the isolated nucleic acidi in "antisense" therapy. As used herein, "antisense" therapy refers to administration or in situ generation of oligonucleotide molecules or their derivatives which specifically hybridize (e.g., bind) under cellular conditions, with the cellular mRNA and/or genomic DNA encoding one or more of the subject MCP-5 proteins so as to inhibit expression of that protein, e.g., by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a MCP-5 protein. Alternatively, the antisense construct is an oligonucleotide probe which is generated ex vivo and which, when introduced into the cell causes inhibition of expression by hybridizing with the mRNA and/or genomic sequences of a MCP-5 gene. Such oligonucleotide probes are preferably modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S.

Pat. Nos. 5,176,996; 5,264,564; and 5,256,775). Additionally, general approaches to constructing oligomers useful in antisense therapy have been reviewed, for example, by Van der Krol et al. (1988) Biotechniques 6:958–976; and Stein et al. (1988) Cancer Res 48:2659–2668. With respect to antisense DNA, oligodeoxyribonucleotides derived from the translation initiation site, e.g., between the −10 and +10 regions of the MCP-5 nucleotide sequence of interest, are preferred.

Antisense approaches involve the design of oligonucleotides (either DNA or RNA) that are complementary to MCP-5 mRNA. The antisense oligonucleotides will bind to the MCP-5 mRNA transcripts and prevent translation. Absolute complementarity, although preferred, is not required. a sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex dna may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. Nature 372:333). Therefore, oligonucleotides complementary to either the 5' or 3' untranslated, non-coding regions of a MCP-5 gene could be used in an antisense approach to inhibit translation of endogenous MCP-5 mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of MCP-5 mRNA, antisense nucleic acids should be at least six nucleotides in length, and are preferably less that about 100 and more preferably less than about 50, 25, 17 or 10 nucleotides in length.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single- stranded or double-stranded. the oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxybydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a flirther embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate olgonucleotides can be prepared by use of controlled pore glass polymer supports (Sarin et al., 1988, Proc. Natl. Acad. Sci. U.S.A. 85:7448–7451), etc.

While antisense nucleotides complementary to the MCP-5 coding region sequence can be used, those complementary to the transcribed untranslated region are most preferred.

The antisense molecules can be delivered to cells which express MCP-5 in vivo (e.g., lymph node and thymus). A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it is often difficult to achieve intracellular concentrations of the antisense sufficient to suppress translation on endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous MCP-5 transcripts and thereby prevent translation of the MCP-5 mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al, 1982, Nature 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue; (e.g., for brain, herpesvirus vectors may be used), in which case administration may be accomplished by another route (e.g., systematically).

Ribozyme molecules designed to catalytically cleave MCP-5 mRNA transcripts can also be used to prevent translation of MCP-5 mRNA and expression of MCP-5 (See, e.g., PCT International Publication WO90/11364, published Oct. 4, 1990; Sarver et al., 1990, Science 247:1222–1225 and U.S. Pat. No. 5,093,246). While ribozymes that cleave mRNA at site specific recognition sequences can be used to destroy MCP-5 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. There are a number of potential hammerhead ribozyme cleavage sites within the nucleotide sequence of human MCP-5 cDNA (FIG. 1). Preferably the ribozyme is engineered so that the cleavage recognition site is located near the 5' end of the MCP-5 mRNA; ie., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a MCP-5 gene.

As in the antisense approach, the ribozymes can be composed of modified oligonucleotides (e.g., for improved stability, targeting, etc.) and should be delivered to cells which express the MCP-5 gene in vivo. A preferred method of delivery involves using a DNA construct "encoding" the robozyme under the control of a strong constitutive pol III or pol II promoter, so that transfected cells will produce sufficient quantities of the ribozyme to destroy endogenous MCP-5 messages and inhibit translation. Because ribozymes unlike anisense molecules, are catalytic, a lower intracellular concentration is required for efficiency.

Endogenous MCP-5 gene expression can also be reduced by inactivating or "knocking out" the MCP-5 gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional MCP-5 (or a completely unrelated DNA sequence) flanked by DNA homologous to the endogenous MCP-5 gene (either the coding regions or regulatory regions of the MCP-5 gene) can be used, with or without a selectable marker and/or a negative selectable marker, to transfect cells that express MCP-5 in vivo Insertion of the DNA construct, via targeted homologous recombination, results in inactivation of the MCP-5 gene. Such approaches are particularly suited in the agricultural field where modifications to ES (embryonic stem) cells can be used to generate animal offspring with an inactive MCP-5 (e.g., see Thomas & Capecchi 1987 and Thompson 1989, supra). However this approach can be adapted for use in humans provided the recominant DNA constructs are directly administered or targeted to the required site in vivo using appropriate viral vectors, e.g., herpes virus vectors for delivery to brain tissue; e.g., the hypothalamus and/or choroid plexus.

Alternatively, endogenous MCP-5 gene expression can be reduced by targeting deoxyribonucleotide sequences complementary to the regulatory region of the MCP-5 gene (i.e., the MCP-5 promoter and/or enhancers) to form triple helical structures that prevent transcription of the MCP-5 gene in target cells in the body. (See generally, Helene, C. 1991, Anticancer Drug Des., 6(6):569–84; Helene, C., et al., 1992, Ann, N.Y. Accad. Sci., 660:27–36; and Maher, L. J., 1992, Bioassays 14(12):807–15).

Likewise, the antisense constructs of the present invention, by antagonizing the normal biological activity of one of the MCP-5 proteins, can be used in the manipulation of tissue, e.g., lipid metabolism, both in vivo and for ex vivo tissue cultures.

Furthermore, like the anti-sense techniques (e.g., microinjection of antisense molecules, or transfection with plasmids whose transcripts are anti-sense with regard to a MCP-5 mRNA or gene sequence) antagonizing the normal biological activity of one of the MCP-5 proteins can be used to investigate role of MCP-5 in lipid metabolism. Such techniques can be utilized in cell culture, but can also be used in the creation of transgenic animals, as detailed below.

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA and DNA, ribozme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

4.4. Polypeptides of the Present Invention

The present invention also makes available isolated MCP-5 polypeptides which are isolated from, or otherwise substantially free of other cellular proteins, especially other signal transduction factors and/or transcription factors which may normally be associated with the MCP-5 polypeptide. The term "substantially free of other cellular proteins" (also referred to herein as "contaminating proteins") or "substantially pure or purified preparaions" are defined as encompassing preparations of MCP-5 polypeptides having less than about 20% (by dry weight) contaminating protein, and preferably having less than about 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g., lacking contaminating proteins, or chromatography reagents such as denaturing agents and polymers, e.g., acrylamide or agarose) substances or solutions. In preferred embodiments, purified MCP-5 preparations will lack any contaminating proteins from the same animal from which MCP-5 is normally produced, as can be accomplished by recombinant expression of, for example, a human MCP-5 protein in a non-human cell.

Full length proteins or fragments corresponding to one or more particular motifs and/or domains or to arbitrary sizes, for example, at least 5, 10, 25, 50, 75 and 100, amino acids in length are within the scope of the present invention.

For example, isolated MCP-5 polypeptides can be encoded by all or a portion of a nucleic acid sequence shown in any of SEQ ID Nos. 1 or 3. Isolated peptidyl portions of MCP-5 proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a MCP-5 polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-tppe (e.g., "authentic") MCP-5 protein.

Another aspect of the present invention concerns recombinant forms of the MCP-5 proteins. Recombinant polypeptides preferred by the present invention, in addition to native MCP-5 proteins (e.g., as set forth in SEQ ID No. 3), are encoded by a nucleic acid, which is at least 85% homologous and more preferably 90% homologous and most preferably 95% homologous with an amino acid sequence represented by SEQ ID No: 2 or encoded by SEQ ID NOs. 1 or 3. Polypeptides which are encoded by a nucleic acid that is at least about 98–99% homologous with the sequence of SEQ ID Nos: 1 or 3 or which are 98–99% homologous with the amino acid sequence set forth in SEQ ID No. 2 are also within the scope of the invention. In a preferred embodiment, a MCP-5 protein of the present invention is a mammalian MCP-5 protein. In a particularly preferred embodiment a MCP-5 protein is set forth as SEQ ID No: 2. In particularly preferred embodiment, a MCP-5 protein has a MCP-5 bioactivity. It will be understood that certain post-translational modifications, e.g., phosphorylation and the like, can increase the apparent molecular weight of the MCP-5 protein relative to the unmodified polypeptide chain.

The present invention further pertains to recombinant forms of one of the subject MCP-5 polypeptides. Such recombinant MCP-5 polypeptides preferably are capable of functioning in one of either role of an agonist or antagonist of at least one biological activity of a wild-type ("authentic") MCP-5 protein of the appended sequence listing. The term "evolutionarily related to", with respect to amino acid sequences of MCP-5 proteins, refers to both polypeptides having amino acid sequences which have arisen naturally, and also to mutational variants of human MCP-5 polypeptides which are derived, for example, by combinatorial mutagenesis.

In general, polypeptides referred to herein as having an activity (e.g., are "bioactive") of a MCP-5 protein are defined as polypeptides which include an amino acid sequence encoded by all or a portion of the nucleic acid sequences shown in one of SEQ ID Nos: 1 or 3 and which mimic or antagonize all or a portion of the biological/biochemical activities of a naturally occurring MCP-5 protein. Examples of such biological activity include the ability to modulate inflammation. Other biological activities of the subject MCP-5 proteins are described herein or will be reasonably apparent to those skilled in the art. According to the present invention, a polypeptide has biological activity if it is a specific agonist or antagonist of a naturally-occurring form of a MCP-5 protein.

The present invention further pertains to methods of producing the subject MCP-5 polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant MCP-5 polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant MCP-5 polypeptide is a fusion protein containing a domain which facilitates its purification, such as GST fusion protein.

Moreover, it will be generally appreciated that, under certain circumstances, it may be advantageous to provide homologs of one of the subject MCP-5 polypeptides which function in a limited capacity as one of either a MCP-5 agonist (mimetic) or a MCP-5 antagonist, in order to promote or inhibit only a subset of the biological activities of the naturally-occurring form of the protein. thus, specific biological effects can be elicited by treatment with a homolog of limited function, and with fewer side effects relative to treatment with agonists or antagonists which are directed to all of the biological activities of naturally occurring forms of MCP-5 proteins.

Homologs of each of the subject MCP-5 proteins can be generated by mutagenesis, such as by discrete point mutation(s), or by truncation For instance, mutation can give rise to homologs which retain substantially the same, or merely a subset, of the biological activity of the MCP-5 polypeptide from which it was derived. Alternatively, antagonistic forms of the protein can be generated which are able to inhibit the function of the naturally occurring form of the protein, such as by competitively binding to a downstream or upstream member of the MCP-5 cascade which includes the MCP-5 protein. In addition, agonistic forms of the protein may be generated which are constitutively active. Thus, the MCP-5 protein and homologs thereof provided by the subject invention may be either positive or negative regulators of weight control and/or diabetes.

The recombinant MCP-5 polypeptides of the present invention also include homologs of the wildtype MCP-5 proteins, such as versions of those protein which are resistant to proteolytic cleavage, as for example, due to mutations which alter ubiquitination or other enzymatic targeting associated with the protein.

MCP-5 polypeptides may also be chemically modified to create MCP-5 derivatives by forming covalent or aggregate conjugates with other chemical moieties, such as glycosyl groups, lipids, phosphate, acetyl groups and the like. Covalent derivatives of MCP-5 proteins can be prepared by linking the chemical moieties to functional groups on amino acid sidechains of the protein or at the N-terminus or at the C-terminus of the polypeptide.

Modification of the structure of the subject MCP-5 polypeptides can be for such purposes as enhancing therapeutic or prophylactic efficacy, stability (e.g., ex vivo shelf life and resistance to proteolytic degradation in vivo), or post-translational modifications (e.g., to alter phosphorylation pattern of protein). Such modified peptides, when designed to retain at least one activity of the naturally-occurring form of the protein, or to produce specific antagonists thereof, are considered functional equivalents of the MCP-5 polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a senne, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur—containing=cysteine and methionine. (see, for example, *Biochemistry*, 2nd ed., Ed. by L. Stryer, WH Freeman and Co.: 1981). Whether a change in the amino acid sequence of a peptide results in a finctional MCP-5 homolog (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention frtther contemplates a method for generating sets of combinatorial mutants of the subject MCP-5 proteins as well as truncation mutants, and is especially usefuil for identifing potential variant sequences (e.g., homologs). The purpose of screening such combinatorial libraries is to generate, for example, novel MCP-5 homologs which can act as either agonists or antagonist, or alternatively, possess novel activities all together. Thus, combinatorially-derived homologs can be generated to have an increased potency relative to a naturally occurring form of the protein.

Likewise, MCP-5 homologs can be generated by the present combinatorial approach to selectively inhibit (antagonize) induction by a lipid. For instance, mutagenesis can provide MCP-5 homologs which are able to bind other signal pathway proteins (or DNA) yet prevent propagation of the signal, e.g., the homologs can be dominant negative mutants. Moreover, manipulation of certain domains of MCP-5 by the present method can provide domains more suitable for use in fusion proteins.

In one embodiment, the variegated library of MCP-5 variants is generated by combinatorial mutagenesis at the nucleic acid level, and is encoded by a variegated gene library. For instance, a mixture of synthetic oligonucleotides can be enzymatically ligated into gene sequences such that the degenerate set of potential MCP-5 sequences are expressible as individual polypeptides, or alternatively, as a set of larger fusion proteins (e.g., for phage display) containing the set of MCP-5 sequences therein.

There are many ways by which such libraries of potential MCP-5 homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential MCP-5 sequences. The synthesis of degenerate oligonucleotides is well known in the art (see for example, Narang, SA (1983) *Tetrahedron* 39:3; Itakura et al. (1981) *Recombinant DNA, Proc 3rd Cleveland Sympos. Macromolecules*, ed. A G Walton, Amsterdam: Elsevier pp 273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Likewise, a library of coding sequence fragments can be provided for a MCP-5 clone in order to generate a variegated population of MCP-5 fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a MCP-5 coding sequence with a nuclease under conditions wherein nicking occurs only about once per molecule; (ii) denaturing the double stranded DNA; (iii) renaturing the DNA to form double stranded DNA which can include senselantisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of MCP-5 homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate MCP-5 sequences created by combinatorial mutagenesis techniques.

In one embodiment, cell based assays can be exploited to analyze the variegated MCP-5 library. For instance, the library of expression vectors can be transfected into a cell line. The transfected cells are then contacted with the insulin and the effect of the MCP-5 mutant on signaling by a Y5 receptor can be detected.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a usefuil sampling of sequence space. REM is an algorithm which enhances the frequency of functional mutants in a library when an appropriate selection or screening method is employed (Arkin and Yourvan, 1992, *PNAS USA* 89:7811–7815; Yourvan et al., 1992, *Parallel Problem Solving from Nature*, 2., In Maenner and Manderick, eds., Elsevir Publishing Co., Amsterdam, pp. 401–410; Delgrave et al., 1993, *Protein Engineering* 6(3):327–331).

The invention also provides for reduction of the MCP-5 proteins to generate mimetics, e.g., peptide or non-pepide agents, which are able to disrupt binding of a MCP-5 polypeptide of the present invention with either upstream or downstream components, such as binding proteins or interactors. Thus, such mutagenic techniques as described above are also useful to map the determinants of the MCP-5 proteins which participate in protein-protein interactions involved in, for example, binding of the subject MCP-5 polypeptide to its receptor. To illustrate, the critical residues of a subject MCP-5 polypeptide which are involved in molecular recognition of its receptor can be determined and used to generate MCP-5-derived peptidomimetics which competitively inhibit binding of the authentic MCP-5 protein with that moiety. By employing, for example, scanning mutagenesis to map the amino acid residues of each of the subject MCP-5 proteins which are involved in binding other extracellular proteins, peptidomimetic compounds can be generated which mimic those residues of the MCP-5 protein which facilitate the interaction. such mimetics may then be used to interfere with the normal finction of a MCP-5 protein. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffinan et al. in *Peptides: Chemistry and Biology*, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

4.4.1. Cells Expressing Recombinant MCP-5 Polypeptides

This invention also pertains to host cells transfected to express a recombinant form of the subject MCP-5 polypeptides. The host cell may be any prokaryotic or eukaryotic cell. Thus, a nucleotide sequence derived from the cloning of mammalian MCP-5 proteins, encoding all or a selected portion of the full-length protein, can be used to produce a recombinant form of a MCP-5 polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g., MAP kinase, p53, WT1, PTP phosphotases, SRC, and the like. Similar procedures, or modifications thereof, can be employed to prepare recombinant MCP-5 polypeptides by microbial means or tissue-culture technology in accord with the subject invention.

The recombinant MCP-5 genes can be produced by ligating a nucleic acid encoding a MCP-5 protein, or a portion thereof, into a vector suitable for expression in either prokaryotic cells, eukaryotic cells, or both. Expression vectors for production of recombinant forms of the subject MCP-5 polypeptides include plasmids and other vectors. For instance, suitable vectors for the expression of a MCP-5 polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, a MCP-5 polypeptide is produced recombinantly utilizing an expression vector generated by sub-cloning the coding sequence of one of the MCP-5 genes represented in SEQ ID Nos:1 or 3.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

In some instances, it may be desirable to express the recombinant MCP-5 polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a MCP-5 protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing MCP-5-derived polypeptides in a host which produces MAP (e.g., *E. coli* or CM89 or *S. cerevisiae*), or in vitro by use of purified MAP (e.g., procedure of Miller et al., supra).

In other embodiments transgenic animals, described in more detail below could be used to produce recombinant proteins.

4.4.2 Fusion Proteins and Immunogens

In another embodiment, the coding sequences for the polypeptide can be incorporated as a part of a fusion gene including a nucleotide sequence encoding a different polypeptide. This type of expression system can be useful under conditions where it is desirable to produce an immunogenic fragment of a MCP-5 protein. For example, the VP6 capsid protein of rotavirus can be used as an immunologic carrier protein for portions of the MCP-5 polypeptide, either in the monomeric form or in the form of a viral particle. The nucleic acid sequences corresponding to the portion of a subject MCP-5 protein to which antibodies are to be raised can be incorporated into a fusion gene construct which includes coding sequences for a late vaccinia virus structural protein to produce a set of recombinant viruses expressing fusion proteins comprising MCP-5 epitopes as part of the virion. it has been demonstrated with the use of immunogenic fusion proteins utilizing the Hepatitis B surface antigen fusion proteins that recombinant Hepatitis B virions can be utilized in this role as well. Similarly, chimeric constructs coding for fuision proteins containing a portion of a MCP-5 protein and the poliovirus capsid protein can be created to enhance immunogenicity of the set of polypeptide antigens (see, for example, EP Publication No: 0259149; and Evans et al. (1989) *Nature* 339:385; Huang et al. (1988) *J. Virol.* 62:3855; and Schlienger et al. (1992) *J. Virol.* 66:2).

The Multiple antigen peptide system for peptide-based immunization can also be utilized to generate an immunogen, wherein a desired portion of a MCP-5 polypeptide is obtained directly from organo-chemical synthesis of the peptide onto an oligomeric branching lysine core (see, for example, Posnett et al. (1988) *JBC* 263:1719 and Nardelli et al. (1992) *J. Immunol.* 148:914). Antigenic determinants of MCP-5 proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the MCP-5 polypeptides of the present invention. For example, MCP-5 polypeptides can be generated as glutathione-S-transferase (GST-fusion) proteins. Such GST-fusion proteins can enable easy purification of the MCP-5 polypeptide, as for example by the use of glutathione-derivatized matrices (see, for example, *Current Protocols in Molecular Biology*, eds. Ausubel et al. (N.Y.: John Wiley & Sons, 1991)).

In another embodiment, a fusion gene coding for a purification leader sequence, such as a poly-(His)/enterokinase cleavage site sequence at the N-terrninus of the desired portion of the recombinant protein, can allow purification of the expressed fusion protein by affinity chromatography using a $Ni^{2+}$ metal resin. The purification leader sequence can then be subsequently removed by treatment with enterokinase to provide the purified protein (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

4.4.3. Antibodies

Another aspect of the invention pertains to an antibody specifically reactive with a mammalian MCP-5 protein. For example, by using immunogens derived from a MCP-5 protein, e.g., based on the cDNA sequences, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal, such as a mouse, a hamster or rabbit can be immunized with an immunogenic form of the peptide (e.g., a mammalian MCP-5 polypeptide or an antigenic fragment which is capable of eliciting an antibody response, or a fusion protein, as described above). Techniques for conferring immunogenicity on a protein or peptide include conjugation to carriers or other techniques well known in the art. An immunogenic portion of a MCP-5 protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a MCP-5 protein of a mammal, e.g., antigenic determinants of a protein set forth in SEQ ID No: 2 or closely related homologs (e.g., at least 90% homologous, and more preferably at least 94% homologous).

Following immunization of an animal with an antigenic preparation of a MCP-5 polypeptide, anti-MCP-5 antisera can be obtained and, if desired, polyclonal anti-MCP-5 antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) *Nature*, 256: 495–497), the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemnically for production of antibodies specifically reactive with a mammalian MCP-5 polypeptide of the present invention and monoclonal antibodies isolated from a culture comprising such hybridoma cells. In one embodiment anti-human MCP-5 antibodies specifically react with the protein encoded by the DNA of ATCC® deposit No. 98172.

The term antibody as used herein is intended to include fragments thereof which are also specifically reactive with one of the subject mammalian MCP-5 polypeptides. Antibodies can be fragmented using conventional techniques and the fragments screened for utility in the same manner as described above for whole anibodies. For example, $F(ab)_2$ fragments can be generated by treating antibody with pepsin. The resulting $F(ab)_2$ fragment can be treated to reduce disulfide bridges to produce Fab fragments. The antibody of the present invention is fiwther intended to include bispecific, single-chain and chimeric molecules having affinity for a MCP-5 protein conferred by at least one CDR region of the antibody. In preferred embodiments, the anibodies, the antibody further comprises a label attached thereto and able to be detected, (e.g., the label can be a radioisotope, fluorescent compound, enzyme or enzyme co-factor).

Antibodies which specifically bind MCP-5 epitopes can also be used in immunohistochemical staining of tissue samples in order to evaluate the abundance and pattern of expression of each of the subject MCP-5 polypeptides. Anti-MCP-5 antibodies can be used diagnostically in immuno-precipitation and irnmuno-blotting to detect and evaluate MCP-5 protein levels in tissue as part of a clinical testing procedure. For instance, such measurements can be useful in predictive valuations of the onset or progression of proliferative disorders. Likewise, the ability to monitor MCP-5 protein levels in an individual can allow determination of the efficacy of a given treatment regimen for an individual afflicted with such a disorder. The level of MCP-5 polypeptides may be measured from cells in bodily fluid, such as in samples of cerebral spinal fluid, such as produced by biopsy. Diagnostic assays using anti- MCP-5 antibodies can include, for example, immunoassays designed to aid in early diagnosis of an inflammatory disorder Another application of anti-MCP-5 antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a MCP-5 protein, e.g., other orthologs of a particular MCP-5 protein or other paralogs from the same species, can then be detected with antibodies, as, for example, reacting nitrocellulose filters lifted from infected plates with anti-MCP-5 anibodies. Posiive phage detected by this assay can then be isolated from the infected plate. Thus, the presence of MCP-5 homologs can be detected and cloned from other animals, as can alternate isoforms (including splicing variants) from humans.

4.5 Methods of Treating Disease

There are a wide variety of disorders for which MCP-5 molecules of the present invention can be used in treatment. As discussed herein, MCP-5 proteins and polypeptides described herein stimulate chemotaxis of eosinophils, monocytes and lymphocytes, but not neutrophils and are thus likely to be involved with eosinophil-, monocyte- and/or lymphocyte- mediated inflammations.

Given a subjects' particular condition, it will be desirable to either enhance chemotactic responses by upregulating MCP-5 bioactivity or reduce inflammation by down regulating MCP-5 bioactivity.

Accordingly, the MCP-5 modulating agents described herein will have a wide range of applications in enhancing chemotactic responses. Monocytes are important mediators of cell-mediated immunity and are important in the presentation of antigen to T cells. Therefore, MCP-5 agonist would be useful to adminster in conjunction with an antigen or DNA encoding an antigen (e.g. a vaccine). The recruitment of monocytic infiltrates is desirable in the case of infection, for example, with a bacterial, fungal or parasitic agent. Macrophages also mediate antibody-dependent cellular cytotoxicity (ADCC) reactions, which have been shown to be important in tumor cell killing. Since MCP-5 also recruits lymphocytes, it will be desirable to upregulate MCP-5 bioactivity to attract either B cells or T cells to the site of an infection. Therefore MCP-5 modulating agents that up regulate would be useful in promoting wound healing, for example, MCP-5 has also been shown to be chemotactic for eosinophils, which are known to play an important role in the immune responses to parasitic infections, such as in schistosomiasis.

In other cases it will be desirable to down regulate MCP-5 bioactivity. For example, to limit an unwanted inflammatory response or an allergic response. Down modulation of MCP-5 will be useful in preventing unwanted inflammation in a variety of organ systems. For example, in the colon MCP-5 can be down modulated to reduce the symptoms of inflammatory bowel disease. Modulation of MCP-5 can be used to treat inflammation of the kidney, e.g., glomerular inflammation or lupus membranous nephropathy, glomerulo-sclerosis, or A nephropathy. In the liver MCP-5 can be used to control hepatic inflammation, such as that induced by LPS. In the lung, MCP-5 modulation can reduce the symptoms associated with fibrotic lung disease, idiopathic pulmonary disease, adult respiratory distress syndrome, sarcoidosis, pleural effusions which occur secondary to various diseases, respiratory allergies, and asthmna.

Adherence of monocytes to the endothelium of vessels and their migration into the subendothelial space is an important early event in the pathogenesis of atherosclerosis. Thus, modulation of MCP-5 will be useful in reducing the symptoms associated with atherosclerosis and heart disease.

Likewise, MCP-5 modulation will be usefull in the control of granuloma formation, endometriosis, gingival inflammation, inflammatory skin conditions, delayed-type hypersensitivity responses, and allergic inflammation. MCP-5 is also likely to be involved in the recruitment of cells to the arthritic joint. Therefore, modulation of MCP-5 should also be of benefit in the treatment of arthritis.

4.5.1. Effective Dose

Toxicity and therapeutic efficacy of such compounds can be determined by standard pharmaceutical procedures in cell cultures or experimental animals, e.g., for determining The $Ld_{50}$ (The Dose Lethal To 50% Of The Population) And The $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (ie., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.5.2. Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the oligomers of the invention can be formulated for a variety of loads of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's soluion. In addition, the oligomers may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternaively, the acive ingredient may be in powder form for constitution with a suitable vehicle, e.g, sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

In clinical settings, the gene delivery systems for the therapeutic MCP-5 gene can be introduced into a patient by any of a number of methods, each of which is familiar in the art. For instance, a pharmaceutical preparation of the gene delivery system can be introduced systemically, eg., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) *PNAS* 91: 3054–3057). A MCP-5 gene, such as any one of the sequences represented in the group consisting of SEQ ID NOs 1–6 or a sequence homologous thereto can be delivered in a gene therapy construct by electroporation using techniques described, for example, by Dev et al. ((1994) *Cancer Treat Rev* 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g., retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4.6 Diagnostic and Prognostic Assays

In the diagnostic and prognostic assays described herein, in addition to the MCP-5 nucleic acid molecules and polypeptides described above, the present invention provides for the use of nucleic comprising at least a portion of a MCP-5 nucleic acid molecule, for example, at least a portion of a nucleic acid sequence shown in SEQ ID Nos: 1 or 3 or polypeptides as shown in SEQ ID No 2.

The present method provides a method for determining if a subject is at risk for an inflammatory disorder. In preferred embodiments, the methods can be characterized as comprising detecting, in a sample of cells from the subject, the presence or absence of a genetic lesion characterized by at least one of (i) an alteration affecting the integrity of a gene encoding a MCP-5-protein, or (ii) the mis-expression of the MCP-5 gene. To illustrate, such genetic lesions can be detected by ascertaining the existence of at least one of (i) a deletion of one or more nucleotides from a MCP-5 gene, (ii) an addition of one or more nucleotides to a MCP-5 gene, (iii) a substitution of one or more nucleotides of a MCP-5 gene, (iv) a gross chromosomal rearrangement of a MCP-5 gene, (v) a gross alteration in the level of a messenger RNA transcript of a MCP-5 gene, (vii) aberrant modification of a MCP-5 gene, such as of the methylation pattern of the genomic DNA, (vii) the presence of a non-wild type splicing pattern of a messenger RNA transcript of a MCP-5 gene, (viii) a non-wild type level of a MCP-5-protein, (ix) allelic loss of a MCP-5 gene (x) inappropriate post-translational modification of a MCP-5-protein and (xi) errors and mutations in the promoter, which result in aberrant expression. As set out below, the present invention provides a large number of assay techniques for detecting lesions in a MCP-5 gene, and importantly, provides the ability to discern between different molecular causes underlying MCP-5-dependent inflammation.

In an exemplary embodiment, there is provided a nucleic acid composition comprising a (purified) oligonucleotide probe including a region of nucleotide sequence which is capable of hybridizing to a sense or antisense sequence of a MCP-5 gene, such as represented by any of SEQ ID Nos: 1 or 3, or naturally occurring mutants thereof, or 5' or 3' flanking sequences or intronic sequences naturally associated with the subject MCP-5 genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

As set out above, one aspect of the present invention relates to diagnostic assays for determining, in the context of cells isolated from a patient, if mutations have arisen in one or more MCP-5 of the sample cells. The present method provides a method for determining if a subject is at risk for an inflammatory disorder. In preferred embodiments, the method can be generally characterized as comprising detecting, in a sample of cells from the subject, the presence or absence of a genetic lesion characterized by an alteration affecting the integrity of a gene encoding a MCP-5. To illustrate, such genetic lesions can be detected by ascertaining the existence of at least one of (i) a deletion of one or more nucleotides from a MCP-5-gene, (ii) an addition of one or more nucleotides to a MCP-5-gene, (iii) a substitution of one or more nucleotides of a MCP-5-gene, and (iv) the presence of a non-wild type splicing pattern of a messenger RNA transcript of a MCP-5-gene. As set out below, the present invention provides a large number of assay techniques for detecting lesions in MCP-5 genes.

In certain embodiments, detection of the lesion comprises utilizing the probe/primer in a polymerase chain reacion (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutaions in the MCP-5-gene (see Abravaya et al. (1995) *Nuc Acid Res* 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a MCP-5 gene under conditions such that hybridization and amplification of the MCP-5-gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Another embodiment of the invention provides for a nucleic acid composition comprising a (purified) oligonucleotide probe including a region of nucleotide sequence which is capable of hybridizing to a sense or antisense sequence of a MCP-5-gene, or naturally occurring mutants thereof, or 5' or 3' flanking sequences or intronic sequences naturally associated with the subject MCP-5-genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels. Such oligonucleotide probes can be used for both predictive and therapeutic evaluation of allelic mutations which might be manifest in, for example, apoptosis or aberrant cell growth.

The methods described herein may be performed, for example, by utilizing pre-packaged diagnostic kits comprising at least one probe nucleic acid or antibody reagent described herein, which may be conveniently used, e.g, in clinical settings to diagnose patients exhibiting symptoms or family history of a disease or illness involving a MCP-5 gene.

Antibodies directed against wild type or mutant MCP-5 proteins, which are discussed, above, may also be used in disease diagnostics and prognostics. Such diagnostic methods, may be used to detect abnormalities in the level of MCP-5 protein expression, or abnormalities in the structure and/or tissue, cellular, or subcellular location of MCP-5 protein. Structural differences may include, for example, differences in the size, electronegativity, or antigenicity of the mutant MCP-5 protein relative to the normal MCP-5 protein. Protein from the tissue or cell type to be analyzed may easily be detected or isolated using techniques which are well known to one of skill in the art, including but not limited to western blot analysis. For a detailed explanation of methods for carrying out western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of MCP-5 proteins. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the MCP-5 protein, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an anti-MCP-5 protein specific antibody is via linkage to an enzyme and use in an enzyme immunoassay (EIA) (Voller, "The Enzyme Linked Immunosorbent Assay (ELISA)", *Diagnostic Horizons* 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) *Enzyme Immunoassay*, CRC Press, Boca Raton, Fla., 1980; Ishikawa, et al., (eds.) *Enzyme Immunoassay*, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Moreover, it will be understood that any of the above methods for detecting alterations in a MCP-5 gene or gene product can be used to monitor the course of treatment or therapy.

4.7 Transgenic Animals

One aspect of the present invention concerns transgenic animals which are comprised of cells (of that animal) which contain a transgene of the present invention and which preferably (though optionally) express an exogenous MCP-5 protein in one or more cells in the animal. A MCP-5 transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a MCP-5 protein can be essential for many forms of lineage analysis and can additionally provide a means to assess the effects of, for example, lack of MCP-5 expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art.

For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject MCP-5 proteins. For example, excision of a target sequence which interferes with the expression of a recombinant MCP-5 gene, such as one which encodes an antagonistic homolog or an antisense transcript, can be designed to activate expression of that gene. This interference with expression of the protein can result from a variety of mechanisms, such as spatial separation of the MCP-5 gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant MCP-5 protein can be regulated via control of recombinase expression.

Use of the cre/loxP recombinase system to regulate expression of a recombinant MCP-5 protein requires the construction of a transgenic animal containing transgenes encoding both the Cre recombinase and the subject protein. Animals containing both the Cre recombinase and a recombinant MCP-5 gene can be provided through the construction of "double" transgenic animals. A convenient method for providing such animals is to mate two transgenic animals each containing a transgene, e.g., a MCP-5 gene and recombinase gene.

One advantage derived from initially constructing transgenic animals containing a MCP-5 transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic MCP-5 transgene is silent will allow the study of progeny from that founder in which disruption of MCP-5 mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the MCP-5 transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g., a recombinase or a prokaryotic protein, is delivered to the tissue and caused to be expressed, such as in a cell-type specific manner. By this method, a MCP-5 transgene could remain silent into adulthood until "turned on" by the introduction of the transactivator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with H-$2^b$, H-$2^d$ or H-$2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1–2pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a finctional organism.

The number of copies of the transgene constructs which are added to the zygote is dependent upon the total amount of exogenous genetic material added and will be he amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a MCP-5 protein (either agonistic or antagonistic), and antisense transcript, or a MCP-5 mutant. Further, in such embodiments the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*ManipulaMCP-5ng the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J*. 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

In one embodiment, gene targeting, which is a method of using homologous recombination to modify an animal's genome, can be used to introduce changes into cultured embryonic stem cells. By targeting a MCP-5 gene of interest in ES cells, these changes can be introduced into the germlines of animals to generate chimeras. The gene targeting procedure is accomplished by introducing into tissue culture cells a DNA targeting construct that includes a segment homologous to a target MCP-5 locus, and which also includes an intended sequence modification to the MCP-5 genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a MCP-5 gene function through the use of a targeting transgene construct designed to undergo homologous recombination with one or more MCP-5 genomic sequences. The targeting construct can be arranged so that, upon recombination with an element of a MCP-5 gene, a positive selection marker is inserted into (or replaces) coding sequences of the targeted siganlin gene. The inserted sequence functionally disrupts the MCP-5 gene, while also providing a positive selection trait. Exemplary MCP-5 targeting constructs are described in more detail below.

Generally, the embryonic stem cells (ES cells) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) *J. Embryol. Exp. Morphol.* 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934) Still another preferred ES cell line is the WW6 cell line (Ioffe et al. (1995) *PNAS* 92:7357–7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment. A preferred method of insertion is electroporation.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct.

Screening can be accomplished using a variety of methods. Where the marker gene is an antibiotic resistance gene, for example, the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence Alternatively, PCR can be used. Finally, if the marker gene is a gene that encodes an enzyme whose activity can be detected (e.g., β-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the MCP-5 coding sequence, transcriptional regulatory sequence, etc. Typically, less than about 1–5% of the ES cells that take up the knockout construct will actually integrate the knockout construct in the desired location. To identify those ES cells with proper integration of the knockout construct, total DNA can be extracted from the ES cells using standard methods. The DNA can then be probed on a Southern blot with a probe or probes designed to hybridize in a specific pattern to genomic DNA digested with particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, as the appended Examples describe, the transformed ES cells can be microinjected into blastocytes.

The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the MCP-5 gene knocked out in various tissues of the offspring by probing the Western blot with an antibody against the particular MCP-5 protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g., by homologous recombination to insert target sequences, such that tissue specific and/or temporal control of inactivation of a MCP-5-gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and inununology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); Culture Of Animal Cells (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immu-*

*nochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

5. EXAMPLES

5.1 Cloning of Mouse MCP-5

MATERIAL AND METHODS

Mice and in Vivo Procedures.

Eight to ten week old male and female C57BL/6J and RAG-1-deficient mice were purchased from the Jackson Laboratory (Bar Harbor, Me.), and kept in the Center for Blood Research Specific Pathogen Free mouse facility. Ovoalbumin-induced pulmonary eosinophilia (OVA; Sigma, St Louis, Mo.) was generated in these mice as described [Gonzalo, J. A. (1 996) *Immunity* 4:1–14]. Briefly, mice (three individual experiments, n=10) were sensitized by an intraperitoneal (ip.) injection of OVA (0.1 mg/mouse) on day 1, challenged by exposure to aerosolized antigen (2% OVA for 5 min on day 8 and 1% OVA for 20 min on days 15–21). At different times after antigen challenge, mice were euthanized by barbiturate overdose and analyzed. PBS-treated mice (ip and aerosolized) were used as negative controls. RNA was extracted from lungs excised from either OVA-treated wt mice (1, 3, or 6 h after OVA inhalation on days 15, 18 and 21) or OVA-treated RAG-1-deficient mice (3 h after OVA inhalation on days 15, 18 and 21).

Peritoneal recruitment assays in vivo with mMCP-5 protein were performed after i.p. injection of 400 μl or 800 μl of mMCP-5 recombinant protein containing supernatant or control supernatant. At different time points after injection (0, 1, 2, 3, or 4 h), peritoneal lavage with 10 ml of PBS was performed (three individual experiments, n=8–13 for test and control mice per time point and dose). Recovered peritoneal leukocytes were then analyzed and enumerated. For the coinjection experiments, bacterial rmEotaxin (0.5, ug/200 pl per mouse, Peprotech, Inc.) was administered i.p. simultaneously with either 400 μl or 800 μl of mMCP-5 containing supernatant. In one series of experiments, lower doses of Eotaxin (0.2 μg/mouse) were coinjected with lower doses of mMCP-5 (100 μl/mouse). Control mice were injected ip with 1) rmEotaxin protein and control supernatant; 2) PBS and mMCP-5 containing supernatant; 3) PBS and control supernatant. All doses and volumes were exactly the same as these given to test mice. At different time points after coinjection of mMCP-5 containing supernatant and rmEotaxin (1, 2, 3 or 4 h), peritoneal ravage was performed as described above (three individual experiments, n=4–12, for test and control mice per time point and dose) and recovered cells were analyzed.

A partial cDNA fragment of the mMCP-5 gene was cloned from RNA extracted from eosinophilic lungs of OVA-sensitized mice using two degenerate oligonucleotide primers based on conserved regions of the sequence of CC chemokine genes as described previously [Gonzalo, 1996 ibid]. To clone the full-length mouse mMCP-5 cDNA, the same two-step PCR amplification strategy that was employed recently to clone mouse Eotaxin was followed [Gonzalo, 1996 ibid]. In the first step, the 5' region of mMCP-5 cDNA (spanning from the 5' end of the gene to the fragment obtained by degenerate PCR) was obtained by PCR with the primers based on the previously cloned fragment sequences using the 5' RACE strategy. In the second step, the full-length cDNA was amplified by RT-PCR with 5' specific primers, based on the sequences of the cloned 5' region following the same strategy as described above.

The cDNA for these experiments was reverse transcribed from eosinophilic lung RNA and subsequently poly-A tailed following the same procedures as described previously [Gonzalo, 1996 ibid]. Poly-A tailed cDNA was subsequently used as template for PCR with the 5' primer #1 [a chimeric primer containing $(dT)_{17}$ and sequence of the $T_7$ promoter: 5'-TAATACGACTCACTATAGGGATTTTTTTTTTTT TTT)-3' (SEQ ID NO. 4) and the specific 3' primer (5'-CTCCTTATCCAGTATGGTCC-3' (SEQ ID NO 5) based on 75 bp sequence cloned initially by degenerate PCR. A second round of amplification was then performed using the specific 5'-primer #2 (sequence of the $T_7$ promoter 5'-TAATACGACTCACTATAGGG-3' SEQ ID NO 6) and second specific 3' primer (designed nested to first 3'-primer from the sequence of the 75 bp fragment: 5'-ACAGCTTCCCGGGGACACTG-3' SEQ ID NO 7) and 1 μl of the first round PCR products as template. Sequence analysis of the resulting PCR products showed that the cloned 5' fragment did not correspondent to any known genes.

In the second step, the full length cDNA was obtained after two rounds of amplification. In round 1, 1 μl of RT products was generated as described [Gonzalo, 1996 #3874] then used as a template for PCR amplification using primers #1 and gene specific 5' primer (designed from the 5' sequence of the cloned fragment: 5'-AGAGACACTGGTTCCTGAC-3' SEQ ID NO 8). In round 2, products from the first round were used as template for amplification of further specificity using primers #2 and a second gene specific primer (a primer containing sequences nested to first 5'-primer: 5'-TCTCCCTCCACCATGCAGAG-3' SEQ ID NO 9).

Comparison of the Amino Acid Sequence of mMCP-5 Mature Peptide with that of Human and Mouse C-C Chemokines The amino acid sequence of mMCP-5 mature peptide was compared with that of human and mouse C-C chemokines and the phylogenetic tree of human and mouse members of the C-C chemokine family including mMCP-5. The sequences were aligned using the Clustal method with a PAM250 residue weight table and default settings of gap penalties for pairwise and multiple alignments of 3 and 10, respectively (MegAlign, DNASTAR, Madison, Wis.). Amino acid sequences of the mature proteins for the hMCP-1[Li, Y. S. et al. (1993) Mol. Cell. Biochem. 126:61–68; ], hMCP-2 [Van Damme, J. (1992) J Exp Med 176:59–65; ], hMCP-3 [Minty, A. et al. (1993) Eur. Cytokine Netw 4:99–110;], mMCP-1/JE [Kawahara, R. S. (1989) J. Biol. Chem. 264:679–682; ](1 to 85 aa) and mEot [Gonzalo, J. A. (1996) Immunity 4:1–14; ] genes were compared with aminoacid sequence of the putative mature mMCP-5 protein.

Production of Recombinant mMCP-5 Protein in p3X63 Myeloma Cells

The entire coding sequence (from 30 to 450 in the nucleotide sequence) of mMCP-5 cDNA was cloned into the expression vector pEFpuro in the sense orientation [Mizushima, (1990) Nucl. Acids Res 18:5322] and transfected into p3X63 myeloma cells [Karasuyama, (1988) European Journal of Immunology 18:97–104]. Stable transfected cells were made in the selection medium with 10% FCS and subsequently grown for several days in serum-free media (Ultraculture, Biowhittaker, Md.). Serum-free supernatant from cultures of transfected cells was used for the transwell chemotaxis assay and for in vivo induction of leukocyte accumulation. The supernatant of p3X63 cultured cells transfected with the same construct but containing the mMCP-5 cDNA in antisense orientation was used as a control. The same volume of supernatant (mMCP-5-containing, control) was applied to 1 ml Heparin column (Pharmacia), washed and eluted in the volume of 2 ml as recommended by supplier. The eluted solution was dialyzed against 1×PBS overnight at 4° C. [A. Wuyts, (1994) *J. Immunol Methods* 174: 237–247]

In Vitro Chemotaxis

The in vitro migration of leukocytes to recombinant mMCP-5 was evaluated, in duplicate, using a 24-well transweil chamber (Costar, Cambridge, Mass.) [Rot, 1992 #3710]. Various dilutions of tissue culture medium containing mMCP-5 recombinant protein in a final volume of 600 $\mu$l were added into the wells of a 24-well plate. Transwells with 5-mm pores membrane were inserted into each well so that the cells were separated from the control and experimental supernatant samples in the bottom wells. The tested cells were suspended at $2\times10^6$/ml in serum-free medium and 100 $\mu$l of cells was added to the top transwells. Assay plates were incubated for 1 h or for the indicated time periods at 37° C. in 5% $CO_2$. After incubation, the transwells were removed and the number of cells per well counted in the FACScan by passing each sample for a constant predetermined time period. A constant gate was assigned for each leukocyte subpopulation in the SSC/FSC window and was used for every sample When necessary, samples were also stained for cell lineage specific markers and analyzed as explained below. The chemotactic index was calculated as the number of cells that migrated to the sample divided by the number of cells that migrated to the negative control (control supernatant).

Eosinophils were purified from pretoneum of Cadmium-treated IL-5 transgenic mice [Tominaga, (1991) The Journal of Experimental Medicine 173:429–437] using immuno-magnetic depletion of lymphocytes (which are 80–90% of the non-eosinophilic leukocytes in these organs). Briefly, erythrocyte lysed peritoneal cells were labeled with biotin-conjugated anti-Thy (53.2.1) and anti-B220 (6B2) and treated with Streptavidin-coated magnetic beads (m450, Dynal). Eosinophils were enriched by negative selection through a magnetic field. The resulting preparations were 85–95% eosinophils. Macrophages and neutrophils were obtained from the peritoneum after injection of thioglycol-late and percoll gradient separation [Luo, (1994) J. Immunol. 153:4616–4624]. Lymphocytes were obtained from peripheral blood, spleen, lymph nodes or bone marrow after erythrocyte lysis and immunomagnetic depletion of Mac-1+ and Gr-1+ cells as explained above.

Flow cytometry was performed to determine the cell lineage of migratory cells in selected experiments Cells were collected from the bottom chamber of the duplicates of each chemotactic assay, incubated with anti Fc-receptor mAb (2.492, from Pharmingen) and then stained with each one of the following antibodies individually: Gr-1 (8C5), Mac-1 (CD11b), B220 (CD45R), IgM or Thy1.2, conjugated with FITC or PE (Pharmingen). All reactions were performed on ice in PBS with 2% FCS, 2% bovine serum albumin (BSA) and 0.1%, sodium azide. Dead cells were excluded by propidium iodide (Sigma) incorporation. Flow cytometry data were acquired with a FACScan cytometer (Becton Vickinson) and analyzed with CELLQUEST software.

Generation and Screening of Polyclonal Sera and Monoclonal Antibodies

The peptide CADPKEKWVKNSINHLDKTS (SEQ ID NO 11), covering amino acids 74–93 in the mMCP-5 peptide sequence, was synthesized on an automated multiple peptide synthesizer (AMS 422, Abimed) using the solid phase procedure and standard F-moc-chemistry in a base of 25 $\mu$mol. Purity and composition of peptide was confirmed in reverse-phase high performance liquid chromatography and by amino acid analysis using a Beckman 6300 amino acid analyzer. The peptide was then coupled to kehyhole limpet hemocyanin (KLH, Pierce) via its N-terminal cysteine residue using the linking agent sulpho-sucinimidyl 4-(N-maleimido-methyl)cyclohexane-1-carboxylate (sulfo-SMCC) The degree of peptide coupling to carrier was estimated by amino acid analysis of the complex relative to the amino acid analysis of the carrier protein alone.

Polyclonal sera against mMCP-5 was generated according to standard methods [Harlow, (1988) Antibodies: A Laboratory Manual (Cold Spring Harbor, N.Y.: Cold Spring Harbor Press]. Briefly, KLH-coupled mMCP-5 peptide was inoculated into rabbits together with Complete Freunds Adjuvant (CFA) and challenged at different time points after immunization. Antibody titers were determined by ELISA as described below.

Ten-week-old Wistar rats were immunized in the hind, footpad with the KLH-coupled mMCP-5 peptide using a standard protocol used by us previously [Lin, (1995) European Journal of Immunology 25:1508–1516]. 8 days after immunization popliteal lymph nodes were removed and fused with the murine plasmacytoma P3X63Ag8.653 using polyethyleneglycol 4000 (Merck, Germany) as fusing agent, essentially as described [Lin, 1995, supra]. Twelve days after fusion, supernatants from growing wells were screened by EIA for the presence of anti-mMCP-5 antibodies. Positive supernatants were studied in Western blot analysis against mMCP-5 produced by transfected cells. Positive hybridomas were stabilized by limiting dilution using BALB/c mouse thymocytes as a feeder layer until stable antibody production was achieved.

Antibodies from serum and hybridoma culture supernatants were screened using an antigen-coated plate ELISA Microtiter plates (Maxi-sorb, Nunc) were coated with mMCP-5 (73–94) peptides at 3 mg/ml in PBS overnight and ELISA was performed as previously described [Lin, 1995, supra].

Conditioned medium from mMCP-5-transfected cells was electrophoresed under reducing conditions on 17.5% (w/v) SDS-polyacrylamide gels. Gels were transferred to nitrocellulose and incubated with mAb supernatant, followed by a 1/2500 diluted GARat-PO antibody (Dako, Glostrup, Denmark).

Rabbit Polyclonal sera and rat mAbs were shown to recognize a 12 Kd band in a Western blot against mMCP-5-containing supernatant from transfected p3X63 cells. This band was specifically competed by preincubation of the any of the Ab preparations with the mMCP-5 (73–94) peptide used for immunization. Also, this 12 Kd band was not observed when Ab preparation (Polyclonal or monoclonal) were reacted against the supernatant of mock-transfected cells.

20 $\mu$g/mouse of affinity purified anti-mMCP-5 polyclonal antibodies were injected i.v. 30 minutes before OVA challenge from day 15 to day 21 of the OVA treatment. Bronchoalveolar lavage fluid was recovered 3 h after challenge on day 15 or on day 21 and eosinophils enumerated.

Southern and Northern Blots

10 μg of mouse genomic DNA were digested with EcoRI or BamHI or XbaI (New England Biolabs Beverly Mass.), electrophoresed in a 0.8% agarose gel and transferred to a nylon membrane (Genescreen, Dupont) and hybridized with a $^{32}$P-labeled 0.45 Kb mMCP-5 fragment of whole coding sequence cDNA.

Total RNA from the indicated organs of wild type mice, from eosinophilic lungs of OVA-sensitized wt mice (1, 3, and 6h after treatment on days 15, 18 and 21) and from lungs of OVA-treated RAG-1-deficient mice (3 h after challenge on days 15, 18 and 21) was isolated using the guanidinium thiocyanate/acid phenol procedure [Chomczynski, (1987) Anal Biochem 162:156–159]. Northern blots [Sambrook, 1989 ibid] were performed with 20 μg of total RNA from indicated tissues fractionated in a 1.5% agarose/formaldehyde gel and blotted onto a nylon membrane (Genescreen, DuPont). Hybridization and washing were performed as recommended by the supplier. Briefly, membranes were probed using $^{32}$P-labeled mouse probes for mMCP-5 (0.29 Kb fragment cloned from 5' RACE) Eotaxin [Gonzalo, 1996 ibid], RANTES [Heeger, P.(1992) *Kidney Int.* 41:220–226] and MIP-1a [Widmer, U. (1991) *J. Immunol* 146:4031–4040] applied in 50% formamide hybridization solution at 42° C. for 18 h. Blots were also hybridized with β-actin and GAPDH specific probes to verify quantity and quality of RNA.

Measurement of mMCP-5 and mEotaxin mRNA Expression by RT-PCR

For RT-PCR, first strand cDNAs from 111 g of total RNA were generated by reverse transcription with a random hexamer in 20 μl. 1 μl of RT products was then used as the template for PCR amplification using one pair of gene specific primers for 32 or 35 cycles by a step program (94° C., 30 see; 55° C, 30 see; 72° C. 30 see,) on a thermal cycler. The specific mMCP-5 band was resolved at the size of 0.27 kb on a 1.5% agarose gel. The β-actin or GAPDH message was amplified and titrated using specific primers and the same RT products to normalize the amount of input cDNA [Jia, (1995) *European J Immunology* 25:2096–2100] The same amplification without RT template in each reaction was performed as a negative PCR control The specific primers for mMCP-5 used in PCR are as following: 5'-primer, 5'-TCTCCCTCCACCAIGCAGAG-3' (SEQ ID NO. 9) and 3'-primer, 5'-CTCCTTATCCAGTATGGTCC-3' (SEQ ID NO. 10). The specific primers for mEot used in PCR are as described before tGonzalo, 1996 ibid].

The macrophage cell lines RAW287 and P388D1 were cultured with TNF-α (20 ng/ml) for 24h and the endothelial cell line bEnd3 and the fibroblast cell line NIH3T3 were cultured with PMA/Ionomycin (10 ng/ml/500 ng/ml) for 8 h Macrophages were freshly isolated from mouse peritoneal cavity 48 hours after injection of thioglycollate (1 ml/mouse) and cultured in vitro with TNF-α (20 ng/ml) or γ-IFN respectively for 24 h.

The mast cells used in studies were from a cloned, growth factor-independent mast cell line (C1.MC/C57.1, [Young, (1987) *Proc. Nat. Acad. Sci. USA* 84:9175–9; Gordon, (1990) *Nature* 346:274; Burd, (1989) *J. Exp. Med.* 170, 245–257) or primary cultures of bone marrow cultured mast cells (BMCMC) C1.MC/C57.1 mast cells were originally derived from bone marrow-cultured mast cells isolated from C57BL/6J mice, which were subsequently cloned by limiting dilution C1.MC/C57.1 mast cells express similar morphological and biochemical characteristics of other reported mouse mast cell lines or primary cultures of mouse bone marrow-derived mast cells [Young, 1987 ibid; Gordon, 1990 ibid]. Primary cultures of BMCMC were derived from bone marrow cells isolated from BALB/c mice and grown in 20% Concanavalin A stimulate spleenconditioned medium for 4–6 weeks as previously described [Young, 1987 ibid; Gordon, 1990 ibid; Burd, 1989 ibid]. BMCMC were used for experiments at 4–6 weeks at which time mast cells represented >99% of the cells as determined by neutral red staining C1.MC/57.1 mast cells were maintained in Dulbecco's Modified Eagle Medium (GIBCO, Grand Island, N.Y.) with 10% heat-inactivated fetal calf serum (Intergen, Purchase, N.Y.), 50~M 2-mercaptoethanol, and 2 mM L-glutamine at 37C in 5% C02.

Immunohistochemical Phenotyping and Quantitation of Leukocytes.

The number and type of migrating leukocytes in response to mMCP-5 recombinant protein or to both chemokines (mMCP-5 recombinant protein and rmEotaxin protein) in peritoneal lavage fluid were determined at the indicated time points. Lavage cells ($5 \times 10^4$) were applied to glass slides by cytocentrifagation and number of eosinophils and neutrophils were enumerated using a sensitive method dependent on the presence of a cyanide-resistant endogenous peroxidase [Gonzalo, 1996 ibid]. To determine the number of lymphocytes, monocytes and macrophages, dried slides were fixed for 10 min in acetone at 4° C. Then, they were stained with mAb directed against Thy 1.2 (53–2.1), CD45R/B220 (RA3-6B2) from PharMingen, (San Diego, Calif.) and Moma-1 (Biosource International, Camarillo, Calif.) using an avidinibiotin staining method. All incubations and washes were carried out as described below. Slides were overlaid with 20% fetal calf serum in PBS for 15 min and incubated for 1 h at RT with the mAbs described above. Bound antibody was visualized by incubation with biotinylated sheep anti-rat immunoglobulin (DAKO, CA) and then with streptavidin peroxidase complex (DAKO, CA) both diluted in 1%, normal mouse serum/PBS (NMS/PBS), and incubated for 30 min. Finally slides were flooded with peroxidase substrate solution (400 mg diaminobenzidine in 10 ml of PBS, containing 0.01% hydrogen peroxide) for 10 min. Control slides were included where monoclonal antibody, biotinylated anti-rat immunoglobulin or Streptavidin complex were selectively omitted. All slides were counterstained with hematoxylin.

Number of leukocyte subtypes was determined in four high power fields (40×magnification; total area 0.5 mm 2) per slide (duplicate slides per mouse and time point were examined). These high power fields were selected randomly under a low power of magnification (4×) at which leukocyte subtypes were not visible and compared with the number of leukocytes present in control mice. Percentage of eosinophils, lymphocytes, monocytes, macrophages, and neutrophils was determined by counting their number as described above and dividing this number by the total number of cells per high power field. To obtain the absolute number of each leukocyte subtype in the lavage, these percentages were multiplied by the total number of cells recovered from the peritoneal fluids.

Immunohistochemical Staining of Lungs and Lymph Nodes for mMCP-5

Lungs from day 21 OVA-treated mice were infused with prewarmed Tissue Tek OCT compound (Cryoform, IEC, Mass.) before being excised, rolled in further OCT and snap frozen in isopentane/dry ice and stored at −70 C Inguinal lymph nodes were isolated from unchallenged mice and processed as above Sections (4μ) were cut onto microscope slides, air dried, fixed in 2% parafornaldehyde (5min, 4° C.) and methanol (10 min, −20 C) Fixed sections from lung and lymph nodes were stained with monoclonal or polyclonal mAb directed against mMCP-5 respectively using an avidin/biotin staining method. Essentially, the same pattern of staining was found with both Ab preparations in every organ tested. However, the staining of the inflamed lung with the anti-MCP5 polyclonal antibodies resulted consistently in a lower signal to noise ratio. All incubations were carried out under humidified conditions and slides were washed twice between steps for 5 min each in 0.1M phosphate buffered saline supplemented with 0.2% gelatin (PBSG). Sections were overlaid with 20% normal rabbit serum (lungs) or 20% normal swine serum (lymph nodes) in PBS for 15 min and then incubated overnight at 4° C. with undiluted monoclonal anti-mMCP-5 (lungs) or polyclonal antimMCP-5 (lymph nodes) at a dilution of 1/500. Endogenous peroxide was subsequently blocked by incubation for 20 min in methanol containing 0.3% hydrogen peroxide.

Non-specific staining due to cross reaction with endogenous avidin or biotin was blocked by incubation with avidin solution followed by biotin solution, both for 20 min. Bound monoclonal antibody was visualized by incubation with biotinylated rabbit anti-rat immunog]obulin (lungs) or biotinylated swine anti-rabbit immunoglobulin (1ymph nodes) both diluted in 10% normal mouse serum PBS, and then streptavidin peroxidase complex prepared according to manufacturer's instructions (all from Dako, Calif.), and incubated for one hour. Finally, slides were flooded with peroxidase substrate solution (400mg diaminobenzidine in 10 ml PBS, containing 0.01% hydrogen peroxide) for 10 min before counter staining with hematoxylin. Control sections were included where monoclonal antibody, biotinylated anti-rat immunoglobulin or streptavidin complex were selectively omitted. Control slides of lung were also stained with a negative isotype matched hybridoma and lymph nodes with pre-immune rabbit serum instead of primary antibody.

Reduction of OVA-induced Lung Eosinophilia by Anti-mMCP-5 Blockade in Vivo

Lung eosinophilia was induced by sensitization of mice after an intraperitoneal injection of Ovalbumin (OVA, 0.1. mg/400 ml per mouse) on day 0 of treatment. On day 7 and daily from days 15–21, mice were challenged by exposure to aerosolized OVA (2% OVA for 5 min on day 8 and 1% OVA for 20 min on days 15–21). The lungs (BAL fluid and parenchyma) of the mice subjected to this treatment showed a progressive daily accumulation of eosinophils peaking on day 21. Furthermore, Northern analysis showed that mMCP-5 mRNA is markedly increased in the lungs of these mice during the course of lung eosinophilia. To evaluate the particular contribution of this chemokine to the development of this allergic response, anti-mMCP-5 neutralizing Abs (2-mg/mouse i.v.) were administered 30 min before OVA challenge from day 15 to day 21 of treatment. The same concentration of Rabbit IgG antibody was used as a control.

RESULTS

Cloning, Mapping and Structural Analysis of Mouse MCP-5

To identify novel chemotactic molecules involved in the recruitment of leukocytes to the airways during lung allergic inflammation, degenerated oligonucleotides and PCR were used to clone CC chemokine cDNA sequences. These cDNAs were derived from RNAs extracted from lungs with massive eosinophilia generated after repeated exposure of mice to aerosolized OVA. Three distinct groups of 150 bp-PCR products (including the degenerate primers) with different sequences were obtained using degenerate primers based on the most conserved regions in the CC chemokine gene family. According to the sequence from one of them, one specific primer was designed and 5' RACE cloning strategy was applied to isolate the 5' partial cDNA as described in the Materials and Methods. One band at the size of about 290 bp was cloned from PCR products and sequence analysis showed it included the 75 bp fragment (excluding the degenerate primers) based on which the 5' RACE specific PCR primer was designed. Both nucleotide and predicted amino acid sequences revealed that this cDNA fragment corresponds to a novel gene with homology to CC chemokine family genes present in the Genbank. The complete cDNA for this gene was then cloned using the 3' RACE strategy, which involved two further rounds of nested amplification by PCR with primers based on the nucleotide sequence of the previously cloned 5' fragment. A PCR product of approximately 540 bp was cloned and sequenced, which contained the 290 bp fragment obtained in the 5' RACE experiments. The cloned full-length cDNA for this novel gene contains 540 bp whose nucleotide sequence was confirmed by three independent PCR amplifications It includes an open reading frame of 341 bases encoding a protein of 104 amino acids, a 5' untranslated region of 55 bp, and a 3' untranslated region of 145 bp. The mature protein is composed of 82 amino acids containing five cysteine residues, four of which create the characteristic motif of the CC chemokine family. No potential N-glycosylation sites are present in this protein This cDNA encodes for a novel member of the CC chemokine family with a similarity within the whole coding region of 66.3% to human(h) MCP-1, of 52.7% to mouse (m) MCP-1/JE and of 55.5% to mEotaxin (Eot) at the nucleotide level. Based on its high nucleotide and amino acid similarities with other members of the MCP-subfamily of C-C chemokines as well as because of other features described below, this novel mouse CC chemokine has been called Monocyte Chemotactic Protein-5 (mMCP-5).

Figure 2B:
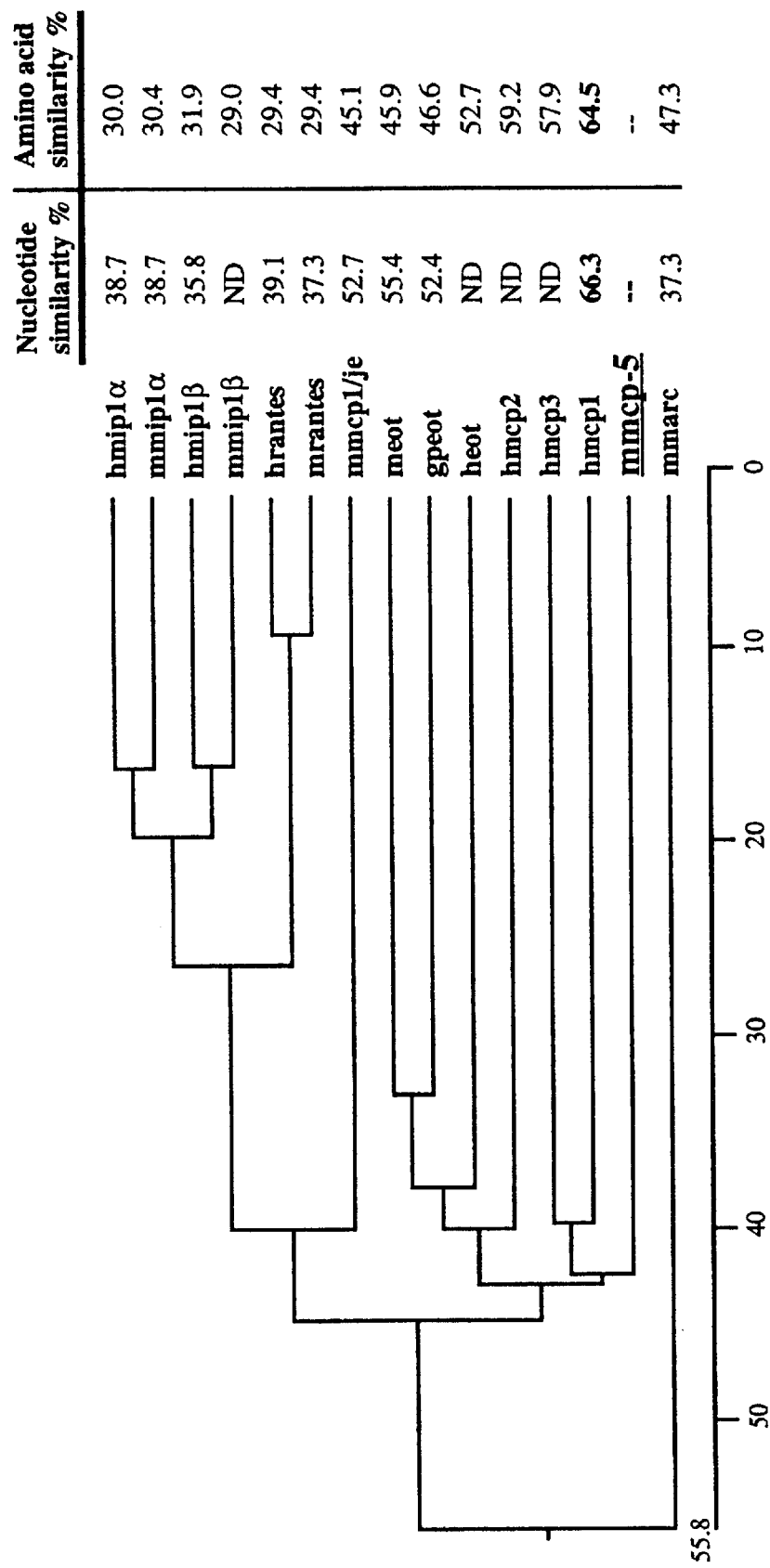

The comparison of the amino acid sequence of mMCP-5 gene with those of other members of the CC chemokine family (FIG. 2A) revealed the highest similarity with members of the human MCP subbranch [Proost, (1996) *J. Leukoc Biol* 59:67–74], especially to hMCP-1 (FIGS. 2.A, B) In addition to the four cysteines, 37 amino acids are completely conserved between mMCP-5 and three hMCPs (FIG. 2A). In spite of these similarities, mMCP-5 has the longer peptide and an additional cysteine on the C-terminus compared to the three human MCPs (FIG. 2A) Comparison of mMCP-5 mature peptide with hMCP-1 mature peptide or with the first 80 aa of the mMCP-1/JE mature peptide revealed 65% and 45% similarity respectively (FIG. 2). mMCP-5 is a basic protein, its theoretical pI is 9.07. The amino acid sequence phylogenetic tree and similarity comparisons with other human or mouse members of CC chemokine family are presented in FIG. 2B. Both showed that mMCP-5 is most similar and evolutionarily related to hMCP-1. The amino acid similarity of mMCP-5 ranges from 29.4 to 64.5% when compared with known C-C chemokines (FIG. 2B).

The mouse chromosomal location of mMCP-5 was determined by interspecific backcross analysis [Copeland, (1991) *Trends Genet.* 7:113–118], and revealed that there is a single gene encoding for this cDNA which is located in the central region of mouse chromosome 11.

To determine the possible existence of a gene homologous to mMCP-5 in humans, a southern blot containing human genomic DNA was hybridized with mMCP-5 cDNA probe. Under conditions of high stringency, a single hybridizing band was detected (which had a different size from that found when the same blot was hybridized with a hMCP-1 probe), suggesting the existence of an mMCP-5 homologue in humans.

FIG. 3 shows the blocking of mMCP-5 protein with specific neutralizing antibodies during the course of OVA-induced allergic inflammation.

In vitro Chemotactic Responses of leukocytes to mMCP-5

To characterize the biofunctional role of mMCP-5, its expression in mammalian cells was engineered. A fragment of the mMCP-5 cDNA containing the fill coding region for the mMCP-5 protein (nucleotides 30 to 450) was inserted into the expression vector pEFpuro and transfected into the myeloma cell line p3X63Ag as described previously [Gonzalo, 1996 ibid]. The stable p3X63Ag transfectants were obtained in 10% FBS-containing tissue culture media in the presence of puromycin. Experimental supernatants from selected transfectants containing recombinant mMCP5 were collected in serum-free media. At the same time, the control supernatants were also obtained, following the same experimental procedures, from the cultured p3X63Ag transfected with the same construct containing the same fragment of mMCP-5 as described above but in opposite orientation with respect to the promoter.

Since mMCP-5 was originally cloned from the eosinophile lung, eosinophil chemotaxis was evaluated first. Eosinophil chemotaxis to mMCP-5 was examined using purified mouse eosinophils (90–95% pure) obtained from the peritoneal cavity of IL-5—transgenic mice [Tominaga, (1991) The Journal of Experimental Medicine 173:429–437] since normal mice do not have appreciable numbers of eosinophils. Supernatant containing mMCP-5 recombinant protein induced migration of eosinophils in a dose-dependent manner compared to the control supernatant. In three independent experiments with different eosinophil and supernatant preparations, recombinant mMCP-5 from undiluted supernatant attracted 10–19% of the input eosinophils in transwell chemotaxis assays. In parallel assays, only 1.1–2.3% of input eosinophils migrated to the control supernatant. As positive control for eosinophil chemotaxis, mEotaxin (mEot) either in bacterial recombinant mEotaxin (br mEot) or as a tissue culture supernatant containing recombinant mEotaxin (prepared from the same cell line, following same procedures described above for mMCP-5, transfected with the same pEF vector, but using the mEot gene) was used in eosinophil transmigration migration assays. 1:10 diluted mEot-containing supernatant (or approximately 150 ng/ml of br mEot) was able to induce the transmigration of ~39% (35–40% migration) of the eosinophil input. A similar degree of eosinophil migration was found when four-fold concentrated (by passage through a heparin column; see methods) mMCP-5-containing supernatant was used in the transwell assays.

To evaluate the chemotactic function of mMCP-5 on lymphocytes, this leukocyte subtype (erythrocyte-lysed, Mac-1 and Gr-1 depleted cells; see methods) was isolated from bone marrow (BM), lymph node (LN), spleen (SP) or peripheral blood (PB) and used for in vitro chemotaxis assays performed as described above. The results from 4 independent experiments performed showed that the supernatant containing mMCP-5 has the ability to induce the migration of lymphocytes from the BM and from the PB. Reproducible chemotaxis of LN or SP-derived lymphocytes to mMCP-5 compared to the control supernatant was not detected. mMCP-5 attracted a subset (~2%) of lymphocytes from both BM and PB. The percentage of lymphocytes that showed chemotaxis to 200 ng/ml of mMIP-1α which was used here as positive control, was similar, but lower than that found for mMCP-5. The chemotactic index of lymphocytes to the undiluted supernatant containing mMCP-5 ranged from 2.5 to 4 in the different experiments, while the index of lymphocytes to mMIP-1α (200 ng/ml) was 2.5–3.0.

Neutrophils and monocytes/macrophages used for in vitro chemotaxis assays were isolated from either normal mouse BM (neutrophils or monocytes) after erythrocyte lysis and Thy1+B220 depletion, from the peritoneal cavity of IL-5 transgenic mice (monocytes) after Gr−1+Thy1+B220 lineage depletion, or from the peritoneum of mice treated previously with thioglycollate (neutrophils or monocytes). Several separate experiments (n=9) with purified populations or enriched cell preparations showed that mMCP-5-containing supernatant elicited concentration-dependent chemotaxis of monocytes isolated from BM, from the peritoneum of IL-5 transgenic mice, or from the peritoneal lavage of mice treated with thioglycollate. This activity was absent in the control supernatant. Although undiluted mMCP-5 containing supernatant only induced the migration of approximately 1.7% of the monocytes, the chemotactic index was 40. mMCP-5 supported the chemotactic migration exclusively of small and non-grandlar monocytes. When analyzed by flow cytometry, the monocyte population that showed chemotaxis to mMCP-5 clustered in a region characterized by the lowest forward and right angle light scatters found among monocytes (defined as Mac1+Gr−1⁻) mMIP-1α, previously reported to be able to attract monocytes [Taub, (1994) Therapeutic Immunology 1:229–246], was used as a positive control in the same experiments. It elicited the transmigration of about 1.3% of the monocytes present in the input population. In these experiments, it was also shown that mMCP-5 has a more potent chemotactic activity than mouse MIP-1α on monocytes, while similar chemotactic activity were shown on macrophages. Neutrophil transmigration assays were performed as described above and showed that there were no significant differences between mMCP-5-containing supernatant and control supernatant in the migration of neutrophils isolated either from BM or from the peritoneal cavity of thioglycollate-treated mice. As positive control, the strong chemotactic response of mouse BM-derived neutrophils to h IL-8 observed in the same experiments was shown.

In vivo Peritoneal Recruitment of Leukocytes to MCP-5

To evaluate the ability of MCP-5 to elicit the recruitment of leukocytes in vivo, the number and type of leukocytes were quantitated in the peritoneal exudates of mice 0, 1, 2, 3 or 4 h after intraperitoneal injection of tissue culture supernatant containing the mMCP-5 recombinant protein or the same volume of the control supernatant. mMCP-5-injected mice showed an increase in the total number of peritoneal cells which maximized 2 h after mMCP-5 recombinant protein injection ($2.3\pm0.2\times10^6$ cells/mouse), when compared with number of cells recovered from the peritoneum of mice injected either with serum-free control supernatant ($1.7\pm0.1\times10^6$ cells/mouse) or PBS ($1.5\pm0.3\times10^6$ cells/mouse). Cells recovered from the peritoneal exudates were subjected to microscope analysis for cell lineage identification. No significant increases in total number of neutrophils or macrophages recovered from the exudates of mMCP-5-injected mice were detected at any time point analyzed when compared with those obtained in control-injected mice. In contrast, a maximum increase in the absolute number of monocytes was observed 2 h after mMCP-5 injection. There was double the number of monocytes 2 h after mMCP-5 injection compared with the number of monocytes recovered from the exudate of mice injected with serum-free control supernatant. Similarly, there was a mMCP-5-induced increase (approximately 1.4-fold) in peritoneal lymphocytes which was not observed in control supernatant-injected mice. As with the total number of lymphocytes, there was a maximal increase in the number of eosinophils 2 h after the administration of the test mMCP-5 protein. Eosinophils increased from $0.25 \pm 0.13 \times 10^5$ of the total cells in the peritoneal exudate of control supernatant-injected mice or PBS-treated littermates to $2.1 \pm 0.6 \times 10^5$ in mMCP-5-containing supernatant injected mice.

Regulation of MCP-5 Expression in the Lung During Allergic Inflammation

Northern analysis showed that increased amounts of mMCP-5 mRNA can be detected in the lung of mice during the course of the experimental induction of lung eosinophilia, using repeated doses of aerosolized OVA for 21 days. This model is characterized by a progressive accumulation of monocytes (maximal at d15) and of lymphocytes and eosinophils, which is maximal at day 21. mMCP-5 mRNA expression peaks 3 h after OVA challenge on the days analyzed. The mRNA expression of mMCP-5 was virtually undetectable 1 h or 6 h after OVA challenge on day 15 but not on days 18 and 21. Similar pattern of mMCP-5 mRNA expression was detected 3 h after OVA administration on the three days analyzed.

Given the central role that lymphocytes play in the development of lung allergic eosinophilia [Walker, (1992) Am. Respir, Dis. 146:109–115], the regulation of mMCP-5 mRNA expression in the lungs of lymphocyte deficient RAG-1 mutant mice [Mombaerts, (1992) Cell 68:869–877)] that were treated with aerosolized OVA for 21 days following the protocol described above was studied. 3 h after challenge on days 15, 18 and 21 of the OVA treatment, total RNA was extracted from the lung of these mice and Northern analyses were performed. There was a strong reduction in the levels of mMCP-5 mRNA at the time points analyzed on days 15 and 18 in OVA-treated RAG-1 mice when compared with OVA-treated wt littermates. The Northern blot also revealed a moderate, but substantial, reduction in the levels of expression of mMCP-5 in the lungs of OVA-treated RAG-1 deficient mice (n=3) 3 h after OVA administration on day 21 of treatment, when compared with that observed in OVA-treated wt mice at the same time point. In contrast, a compatible level of mRNA expression of Eotaxin, RANTES and MIP-1α was found in the lung of mutant and wt mice at any point during the OVA treatment.

To identify the cell type(s) producing mMCP-5 in the allergic lung, immunohistochemical analysis was performed to determine expression. A panel of 10 mAbs was produced to mMCP-5 by immunizing rats with a chemically synthesized mMCP-5 peptide. The screening for specific mAbs was carried out by ELISA and immunohistochemistry of lung and lymph node sections (extensive description of mAbs characterization can be found in the methods section). Immunohistochemical analysis was performed with a representative mAb, ZY2A11, using mouse lung tissue with pronounced eosinophil infiltration. mMCP-5 staining was localized most strongly to smooth muscle cells and to alveolar macrophages. Few, if any, leukocytes forming large perivascular and peribronchiolar infiltrates showed low immunoreactivity. No immunoreactivity to any cell type was recognized in the same tissue using other irrelevant isotype-matched mAbs from the same hybridoma fusion.

In areas of leukocyte localization in the lung tissue, there was an increase in reactivities of macrophages, smooth muscle cells and other tissue resident cells that correlated with the severity of the infiltrate.

Since no significant mMCP-5 immunoreactive protein was produced by infiltrating lymphocytes during the course OVA treatment, the reduction of mMCP-5 mRNA levels in OVA-treated RAG-1 deficient mice indicated a role for lymphocytes in the regulation of mMCP-5 expression by other cell types (i.e macrophages, smooth muscle cells and other resident cells).

To investigate which lymphocyte subtype(s) could be involved in the regulation of mMCP-5 expression, Northern analysis was performed using RNAs from the lungs of mice lacking either T cells and NK-cells (CD3e transgenic-mice) (Wang, B., (1994) Proc Natl. Acad. Sci. USA 91:9402–9406 or CD4+ T cells (CD4-deficient mice) (Rahemtulla, A. et al., (1991) Nature (Lond) 353:180–184) or CD8+ T cells (CD8-deficient mice (Fung-Leung, W.-P et al., (1991) Cell 65:443–449) at the same three time points after OVA-treatment. A comparable level of expression of mMCP-5 mRNA was found in the lungs of these immunodeficient mice when compared with that observed in wild type littermates during OVA-treatment. Similarly, mRNA expression of Eotaxin, RANTES and MIP-1a was not affected by the T-cell deficiency.

To address the regulation of mMCP-5 expression in different lung resident cell types present during allergic eosinophilia, the presence of mRNA for mMCP-5 was evalulated in a limited panel of unstimulated and stimulated cell lines and in freshly isolated cells of different lineages by RT-PCR or Northern.

No expression of mMCP-5 mRNA was found on freshly isolated macrophages by RT-PCR. However, when the macrophages were stimulated in vitro with γ-IFN but not with TNFα, they expressed mMCP-5 mRNA at easily detectable level. Conversely, the same population of freshly isolated peritoneal macrophages stimulated with TNFα, but not γIFN, expressed mRNA for mEotaxin. In agreement with this finding, the expression of mMCP-5 and that of mEot was different in two macrophage cell lines thought two represent two different stages of monocyte/macrophage activation/differentiation Whereas even in the absence of stimulation strong mMCP-5 mRNA expression was found in the macrophage cell line P888D1. No mMCP-5 mRNA could be detected in macrophage cell line RAW287 with or without stimulation. In contrast, of these two macrophage cell lines the only one that expressed detectable mRNA levels of mEot, used here as control, was the RAW287 cell line.

Expression of mMCP-5 mRNA was found in IL3-derived BM mast cell (BMCMC) or in the mast cell line (ClMC/C57.1). In contrast, no mEotaxin mRNA was found in these two mast cell populations. Low, but detectable mRNA levels of mMCP-5 in the endothelial cell line b-End2 were observed with or without stimuli, whereas no mMCP-5 mRNA was detected in non-stimulated or LPS stimulated NIH3T3 fibroblasts. In contrast, both cell lines express detectable levels of mEot mRNA, that are decreased after LPS treatment in vitro, as reported previously [Gonzalo, 1996 ibid]. It is notable also that P388D1 cells expressed much higher levels of mMCP-5 mRNA than b-End2 cells, whereas the opposite was found for the mRNA expression of mEot. The expression of two house-keeping genes, β-actin and GAPDH was studied by RT-PCR on the same RNA samples to control for cDNA input as well as quality.

Role of MCP5 in mEotaxin-induced Eosinophil Recruitment in vivo and in vitro

During the development of lung eosinophilia in response to OVA, several chemokines that share the ability to recruit eosinophils are expressed [Gonzalo, 1996 ibid] Among these, mEotaxin induces the most powerful and specific eosinophil recruiting stimuli [Jose, (1994) J. Exp. Med. 179: 881–887]. To determine if the presence of mMCP-5 in the eosinophilic lung, in which Eotaxin is abundantly expressed, could lead either a larger accumulation of eosinophils or is a possible mechanism to control the inflammatory response, in vivo experiments involving the coinjection of mMCP-5 and Eotaxin recombinant proteins were performed. A standard concentration of Eotaxin (0.5 g/mouse) was coinjected either with 400 $\mu$l/mouse or 800 $\mu$l/mouse of supernatant containing mMCP-5 recombinant protein or with the same volumes of the control supernatant. For comparison, the total number of peritoneal eosinophils recovered from mMCP-5-injected mice or from Eotaxin-injected mice 2 h after injection was $2.2\pm0.6\times10^5$ and $1.3\pm0.5\times10^5$ cells/mouse, respectively. However, when both chemokines were administered simultaneously, the number of infiltrating eosinophils was reduced to $0.8+0.3\times10^5$ cells/mouse. In contrast, when mMCP-5 and mEotaxin were simultaneously administered at very low doses (100 $\mu$l/mouse and 0.2 $\mu$g/mouse, respectively) the number of infiltrating eosinophils ($0.5+0.18\times10^5$ cells/mouse) was greater than those found when mMCP-5 or mEotaxin were injected individually at the same doses ($0.09+0.01\times10^5$ cells/mouse for mMCP-5 and $0.2+0.03\times10^5$ cells/mouse for mEotaxin).

To further understand eosinophil chemotactic responses to combinations of mMCP-5 and mEotaxin in a more controlled experimental system, they were examined in in vitro in the transwell migration assay. The following in vitro experiments were based on the finding that mEot mRNA expression level fluctuate considerably during the OVA treatment in vivo, whereas mMCP-5 mRNA expression remains at almost the same level 3 h after challenged from d15 to d21 by the OVA treatment. Thus, increasing concentrations of mEot in combination with a constant amount of mMCP-5 were used in eosinophil transmigration assays as described above. These experiments revealed that mMCP-5 could enhance in different degrees the migration of eosinophils to mEot (from 3% to 10% in the presence of different concentration of mEot). The maximum enhancement of the mEot-induced eosinophil chemotactic response by mMCP-5 was reproducibly observed when 10 ng/ml of mEot were combined with undiluted mMCP-5 supernatant. As the concentration of mEot was increased from 10 ng/ml to 250 ng/ml in combination with undiluted mMCP-5-containing supernatant in the different experiments, eosinophil migration was enhanced to a lesser extent, until no mMCP-5-induced enhancement of eosinophil chemotaxis was seen at 250 ng/ml of mEotaxin. Furthermore, mMCP-5 reduced mEot-induced eosinophil transmigration in vitro when it was combined with high concentration of mEot (from 50 to 250 ng/ml depending on the experiment). This effect was not observed when the control supernatant was combined with different concentrations of mEot in the same experiments. We have selected two experiments to illustrate that we did observe donor to donor variation in the relative responses to mMCP-5 and mEotaxin, although the pattern discussed above was maintained.

Pattern of Expression of mMCP-5 Under Non-inflammatory Conditions

The distribution of mMCP-5 mRNA expression in mice was examined by Northern blots with approximately an equal amount (15 mg) of total RNA input from different organs. As predicted from the size of the cloned cDNA for mMCP-5, the size of the mRNA transcript was approximately 550 bp. Only lymph node and thymus expressed consistently high levels of mMCP-5 mRNA. mMCP-5 mRNA were also found in heart, skin, lung and spleen by RT-PCR, but no mMCP-5 mRNA was found constitutively in any other tissues of C57BL/6 mice (intestine, brain, kidney, liver, bone marrow and skeletal muscle.

To determine, the cell type(s) responsible for mMCP-5 expression in the lymph node, immunohistochemical analysis of sections of this organ after staining with anti-mMCP-5 antibodies was preformed. mMCP-5 staining was localized to germinal centers of lymphoid follicles. Lymph node stromal cells, including macrophages and follicular dendritic cells were intensely stained with anti-mMCP-5 mAbs. Few, if any, lymphocytes or dendritic cells showed immunoreactivity. As a positive control, lymph node sections were stained with anti-B220 and anti-Thy1 monoclonal antibodies. No immunoreactivity to any cell type was recognized in the same tissue using other irrelevant isotype-matched mAbs from the same hybridoma fusion.

In light of the detection of mMCP-5 in B-cell areas of the lymphoid follicles, the ability of mMCP-5 to elicit chemotaxis of B lymphocytes was tested in vivo and in vitro. Lymphocytes purified from the peripheral blood of mice were subjected to standard transmigration assay. Migratory cells to mMCP-5 were stained either with anti-B220 or anti-Thy1 mAbs, and the proportion of positive cells for each marker was analyzed by flow cytometry. These studies revealed that peripheral blood B-lymphocytes migrated to mMCP-5 in vitro. In fact, B lymphocytes displayed a stronger response to mMCP-5 than T-lymphocytes did, showing a higher chemotactic index. Accordingly, when the proportion of cells expressing these surface markers was analyzed among leukocytes recruited to the peritoneum after injection of mMCP-5, an increase in the number of B-lymphocytes (B220+ cells), but not in the number of T-lymphocytes could be observed. Phenotypic analysis of lymphocytes recovered from the peritoneal exudates of mice 2 h after mMCP-5 injection showed that the increase in peritoneal lymphocyte number is due to the predominant recruitment of IgM+B lymphocytes ($5.7\times10^5\pm0.4\times10^5$ cell/mouse in mMCP-5-injected mice versus $4.4\pm0.1\times10^5$ cell/mouse in serum-free control supernatant-injected mice or $4.1\times10^5\pm0.2\times10^5$ cell/mouse in PBS-treated mice). The number of Thy1.2+ T-lymphocytes remained comparable in these three different groups of experimental mice at the same time point indicated ($5.8\pm2.3\times10^4$; $4.9\pm1.5\times10^4$; and $5.1\pm1.2\times10^4$ in mMCP-5-injected mice, serum-free control supernatant-injected mice and PBS-treated mice respectively.

Reduction of OVA-induced Lung Eosinophilia by Anti-mMCP-5 Blockade In Vivo

Anti-mMCP-5 Abs are able to block the mMCP-5-induced transmigration of eosinophils in vitro. Our results showed that blocking of mMCP-5 in vivo reduced by 77.1% and 27% the number of eosinophils that accumulated in the BAL after OVA challenge on day 15 and day 21, respectively suggesting that mMCP-5 plays a critical role at early stages of this inflammatory response.

5.2 Hybridization of a mMCP-5 Fragment with a Human Genomic Library

Human genomic libraries were screened with mouse probes for a human homologue of mouse MCP-5. A mouse MCP-5 cDNA fragment containing murine MCP-5 full length of coding sequence (21–375) bases was labeled by random priming using a kit from Boehringer Mannheim Biochemicals (Indianapolis, Ind.) following the manufacturer's recommended labeling protocol. This probe was used to screen a human lymph node cDNA library using standard molecular biology techniques (Sambrook, Maniatis, Molecular Cloning). Hybridization with the mouse MCP-5 probe was in 6×SSC containing 233 Denhardt's solution and 25 ug/ml denatured salmon sperm DNA overnight at 65° C. The membranes were rinsed twice in 2×SSC, 0.05% SDS at 65° C. followed by two washes (15 min. each) in 0.2×SSC, 0.1% SDS at 55° C. Several phage clone were found to contain a nucleotide sequence with significant similarity to the mouse MCP-5 and were the subjects of further analysis.

5.3 Cloning of Human MCP-5

A human cDNA library made from whole lymph nodes, thymus, spleen, or muscle could be used as a source of human MCP-5. A library expressed in a phage vector would be easiest to screen although one in a plasmid vector could be used as well. Approximately $10^6$ plaques can be screened by filter hybridization, using duplicate filters, with the open reading frame of the mouse cDNA as a $^{32}$P-labelled probe. In practice, this probe is approximately 330 bp and contains the entire mouse cDNA. Hybridization can be done at 42° C. overnight in Nylon Wash (NW) buffer (14% SDS, 130 mM NaHPO$_4$, 14 mM EDTA, and 0.2% Triton-X-100, at pH 7.2). Following hybridization, washes of increasing stringency can be done, starting with 0.5×NW buffer at RT and increasing the temperature to 42° C. An example would be one wash for 20 min. at RT with 0.5×NW buffer followed by a second wash at 42° C. for 10 minutes. Filters are placed on film overnight. Positive hybridizing plaques are picked, replated, and hybridized with probe following the same protocol until they are single clones. The cDNA insert is then sequenced to confirm the identity.

Deposit of Microorganisms

A plasmid containing mMCP-5 was deposited with the American Type Culture Collection Rockville, Md. (ATCC), 10801 Univetsity Boulevard, Massas, Va. 20110-2209 on Sep. 19, 1996 under the terms of the Budapest Treaty and assigned accession number 98172.

---

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 540 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 56..367

(xi) SEQUENCE DESCRIPTION: SEQ ID NO:1:

```
AGAGACACTG GTTCCTGACT CCTCTAGCTT TCATTTCGAA GTCTTTGACC TCAAC ATG        58
                                                              Met
                                                               1

AAG ATT TCC ACA CTT CTA TGC CTC CTG CTC ATA GCT ACC ACC ATC AGT        106
Lys Ile Ser Thr Leu Leu Cys Leu Leu Leu Ile Ala Thr Thr Ile Ser
             5                  10                  15

CCT CAG GTA TTG GCT GGA CCA GAT GCG GTG AGC ACC CCA GTC ACG TGC        154
Pro Gln Val Leu Ala Gly Pro Asp Ala Val Ser Thr Pro Val Thr Cys
         20                  25                  30

TGT TAT AAT GTT GTT AAG CAG AAG ATT CAC GTC CGG AAG CTG AAG AGC        202
Cys Tyr Asn Val Val Lys Gln Lys Ile His Val Arg Lys Leu Lys Ser
     35                  40                  45

TAC AGG AGA ATC ACA AGC AGC CAG TGT CCC CGG GAA GCT GTG ATC TTC        250
Tyr Arg Arg Ile Thr Ser Ser Gln Cys Pro Arg Glu Ala Val Ile Phe
 50                  55                  60                  65

AGG ACC ATA CTG GAT AAG GAG ATC TGT GCT GAC CCC AAG GAG AAG TGG        298
Arg Thr Ile Leu Asp Lys Glu Ile Cys Ala Asp Pro Lys Glu Lys Trp
                 70                  75                  80

GTT AAG AAT TCC ATA AAC CAC TTG GAT AAG ACG TCT CAA ACC TTC ATC        346
Val Lys Asn Ser Ile Asn His Leu Asp Lys Thr Ser Gln Thr Phe Ile
             85                  90                  95
```

```
CTT GAA CCT TCA TGT CTA GGC TGAGAGTTCC AAAAACTCTT ACGTATTTCC         397
Leu Glu Pro Ser Cys Leu Gly *
        100

CCCTGAAGTT CCCCACGGGC AGGGTGATAT TTATTATGAT ATCTAAAAAG AGATGTTTTT    457

AATAATTTAA ACAAACTTGC TTAAATAATA TTTAATGGTA TTTAAGTAAT ATTTGGGCCA    517

ATTAATCCGA ATCTAATTTA AAA                                           540
```

(2) INFORMATION FOR SEQ ID NO:2:

(i) SEQUENCE CHARACTERISTICS:
        (A) LENGTH: 104 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Ile Ser Thr Leu Leu Cys Leu Leu Ile Ala Thr Thr Ile
 1               5                  10                  15

Ser Pro Gln Val Leu Ala Gly Pro Asp Ala Val Ser Thr Pro Val Thr
            20                  25                  30

Cys Cys Tyr Asn Val Val Lys Gln Lys Ile His Val Arg Lys Leu Lys
            35                  40                  45

Ser Tyr Arg Arg Ile Thr Ser Ser Gln Cys Pro Arg Glu Ala Val Ile
    50                  55                  60

Phe Arg Thr Ile Leu Asp Lys Glu Ile Cys Ala Asp Pro Lys Glu Lys
65                  70                  75                  80

Trp Val Lys Asn Ser Ile Asn His Leu Asp Lys Thr Ser Gln Thr Phe
                85                  90                  95

Ile Leu Glu Pro Ser Cys Leu Gly
            100
```

(2) INFORMATION FOR SEQ ID NO:3:

(i) SEQUENCE CHARACTERISTICS:
        (A) LENGTH: 315 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
ATGAAGATTT CCACACTTCT ATGCCTCCTG CTCATAGCTA CCACCATCAG TCCTCAGGTA     60

TTGGCTGGAC CAGATGCGGT GAGCACCCCA GTCACGTGCT GTTATAATGT TGTTAAGCAG    120

AAGATTCACG TCCGGAAGCT GAAGAGCTAC AGGAGAATCA CAAGCAGCCA GTGTCCCCGG    180

GAAGCTGTGA TCTTCAGGAC CATACTGGAT AAGGAGATCT GTGCTGACCC CAAGGAGAAG    240

TGGGTTAAGA ATTCCATAAA CCACTTGGAT AAGACGTCTC AAACCTTCAT CCTTGAACCT    300

TCATGTCTAG GCTGA                                                    315
```

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA -continued

```
    (xi) SEQUENCE DESCRIPTION: SEQ ID NO:4:

TAATACGACT CACTATAGGG ATTTTTTTTT TTTTTT                              36

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CTCCTTATCC AGTATGGTCC                                                20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TAATACGACT CACTATAGGG                                                20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

ACAGCTTCCC GGGGACACTG                                                20

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

AGAGACACTG GTTCCTGAC                                                 19

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

TCTCCCTCCA CCATGCAGAG                                                20
```

```
(2) INFORMATION FOR SEQ ID NO:10:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:10:

Cys Ala Asp Pro Lys Glu Lys Trp Val Lys Asn Ser Ile Asn His Leu
1               5                   10                  15

Asp Lys Thr Ser
            20
```

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. An isolated nucleic acid molecule which hybridizes to the complement of the nucleotide sequence of SEQ ID NO:1 or the complement of the nucleotide sequence of the DNA insert of the plasmid deposited with ATCC as Accession Number 98172 under incubation at 45° C. in 6.0×SSC followed by washing in 0.2×SSC, 0.1% SDS at 65° C.

2. An isolated nucleic acid molecule comprising the nuclceoide sequence of SEQ ID NO:1 or a complement thereof.

3. An isolated nucleic acid molecule comprising the nucleotide sequence of the DNA insert of the plasmid deposited with ATCC as Accession Number 98172 or a complement thereof.

4. An isolated nucleic acid molecule comprising the coding region of the nucleotide sequence of SEQ ID NO:1, or the coding region of the nucleotide sequence of the DNA insert of the plasmid deposited with ATCC as Accession Number 98172 or a complement thereof.

5. An isolated nucleic acid molecule encoding the amino acid sequence of SEQ ID NO:2 or the amino acid sequence encoded by the nucleotide sequence of the DNA insert of the plasmid deposited with ATCC as Accession Number 98172, or a complement thereof.

6. The isolated nucleic acid molecule of claim 5, wherein said nucleic acid molecule encodes the amino acid sequence of SEQ ID NO:2.

7. An isolated nucleic acid molecule encoding the amino acid sequence of SEQ ID NO:2 or the amino acid sequence encoded by the nucleotide sequence of the DNA insert of the plasmid deposited with ATCC as Accession Number 98172 and heterologous amino acid sequences.

8. The isolated nucleic acid molecule of any one of claims 1, 2, 3, 4, 5 or 7, further comprising a label.

9. A method for detecting and/or quantitating a normal or mutated nucleic acid molecule in a sample, comprising the steps of contacting the sample with a nucleic acid molecule of claim 8, and detecting and/or quantitating the label as an indication of the presence and/or amount of the normal or mutated nucleic acid molecule.

10. A vector comprising the coding region of the nucleotide sequence of SEQ ID NO:1 or the coding region of the nucleotide sequence of the DNA insert of the plasmid deposited with ATCC as Accession Number 98172.

11. A vector comprising the nucleotide sequence of SEQ ID NO:1 or the nucleotide sequence of the DNA insert of the plasmid deposited with ATCC as Accession Number 98172.

12. A host cell comprising a vector comprising the nucleotide sequence of SEQ ID NO:1 or the nucleotide sequence of the DNA insert of the plasmid deposited with ATCC as Accession Number 98172.

13. An isolated nucleic acid molecule comprising the nucleotide sequence of SEQ ID NO:1.

14. An isolated nucleic acid molecule comprising the nucleotide sequence of the DNA insert of the plasmid deposited with ATCC as Accession Number 98172.

15. An isolated nucleic acid molecule comprising the coding region of the nucleotide sequence of SEQ ID NO:1, or the coding region of the nucleotide sequence of the DNA insert of the plasmid deposited with ATCC as Accession Number 98172.

16. An isolated nucleic acid molecule encoding the amino acid sequence of SEQ ID NO:2 or the amino acid sequence encoded by the nucleotide sequence of the DNA insert of the plasmid deposited with ATCC as Accession Number 98172.

17. A vector comprising the isolated nucleic acid molecule of any one of claims 13, 14, 15, 16, or 7.

18. The vector of claim 17, which is a recombinant expression vector.

19. An isolated host cell comprising the vector of claim 17.

20. An isolated host cell comprising the recombinant expression vector of claim 18.

21. A method for producing a protein encoded by the nucleic acid molecule of any one of claims 13, 14, 15, 16, or 7 comprising culturing the host cell of claim 20 in a suitable medium until the protein is produced.

22. The method of claim 21, further comprising isolating the protein from the medium or the host cell.

23. An isolated host cell comprising the nucleic acid molecule of any one of claims 13, 14, 15, 16, or 7.

* * * * *